(12) United States Patent
Bischof et al.

(10) Patent No.: US 11,498,889 B1
(45) Date of Patent: Nov. 15, 2022

(54) SELECTIVE 1-HEXENE/1-OCTENE PRODUCTION WITH 1-DECENE

(71) Applicant: Chevron Phillips Chemical Company LP, The Woodlands, TX (US)

(72) Inventors: Steven M. Bischof, Humble, TX (US); James Hillier, Kingwood, TX (US)

( * ) Notice: Subject to any disclaimer, the term of this patent is extended or adjusted under 35 U.S.C. 154(b) by 0 days.

(21) Appl. No.: 17/471,278

(22) Filed: Sep. 10, 2021

(51) Int. Cl.
| | |
|---|---|
| C07C 2/32 | (2006.01) |
| C07C 1/207 | (2006.01) |
| C07C 7/04 | (2006.01) |
| C07C 45/50 | (2006.01) |
| C07C 6/02 | (2006.01) |
| C07C 4/04 | (2006.01) |

(Continued)

(52) U.S. Cl.
CPC ............ *C07C 2/32* (2013.01); *C07C 1/2076* (2013.01); *C07C 4/02* (2013.01); *C07C 4/04* (2013.01); *C07C 4/06* (2013.01); *C07C 5/22* (2013.01); *C07C 5/2206* (2013.01); *C07C 6/02* (2013.01); *C07C 6/04* (2013.01); *C07C 7/04* (2013.01); *C07C 45/50* (2013.01); *C07C 4/22* (2013.01); *C07C 11/107* (2013.01)

(58) Field of Classification Search
CPC .......... C07C 2/32; C07C 1/2076; C07C 4/02; C07C 4/04; C07C 4/06; C07C 5/22; C07C 5/2206; C07C 6/02; C07C 6/04; C07C 7/04; C07C 45/50; C07C 4/22; C07C 11/107
See application file for complete search history.

(56) References Cited

U.S. PATENT DOCUMENTS

| | | |
|---|---|---|
| 8,765,984 B2 | 7/2014 | Upshaw |
| 9,120,826 B1 | 9/2015 | Sydora et al. |

(Continued)

OTHER PUBLICATIONS

John F. Hartwig, "Borylation and Silylation of C—H Bonds: A Platform for Diverse C—H Bond Functionalizations," Accounts of Chemical Research, 2012, vol. 45, No. 6, pp. 864-873.

(Continued)

*Primary Examiner* — Ali Z Fadhel
(74) *Attorney, Agent, or Firm* — Katherine Taconi

(57) ABSTRACT

A process to produce 1-octene and 1-decene includes (a) separating a composition containing an oligomer product—which contains from 15 to 80 mol % $C_6$ olefins, from 20 to 80 mol % $C_8$ olefins, and from 5 to 20 mol % $C_{10}+$ olefins—into a first oligomer composition containing $C_6$ alkanes and at least 85 mol % $C_6$ olefins (e.g., 1-hexene), a second oligomer composition containing at least 85 mol % $C_8$ olefins (e.g., 1-octene), and a heavies stream containing $C_{10}+$ olefins, then (b) contacting a metathesis catalyst system with the first oligomer composition to form a first composition comprising $C_{10}$ linear internal olefins, (c) contacting the $C_{10}$ linear internal olefins with an isomerization hydrofunctionalization catalyst system to form a second composition containing a functionalized alkane, (d) retro-hydrofunctionalizing the functionalized alkane to form a third composition containing 1-decene, and (e) purifying the third composition to isolate a fourth composition containing at least 90 mol % 1-decene. Processes to produce 1-hexene and 1-decene also are described, as well as related manufacturing systems.

30 Claims, 3 Drawing Sheets

(51) Int. Cl.
*C07C 5/22* (2006.01)
*C07C 6/04* (2006.01)
*C07C 4/02* (2006.01)
*C07C 4/06* (2006.01)
*C07C 11/107* (2006.01)
*C07C 4/22* (2006.01)

(56) References Cited

U.S. PATENT DOCUMENTS

| | | | |
|---|---|---|---|
| 10,183,899 B2 | 1/2019 | Bischof | |
| 10,435,334 B2 | 10/2019 | Bischof | |
| 10,723,672 B2 | 7/2020 | Bischof et al. | |
| 2015/0291486 A1* | 10/2015 | Weber | C08F 2/42 585/512 |
| 2016/0303551 A1* | 10/2016 | Zoricak | C07C 2/36 |
| 2016/0375431 A1 | 12/2016 | Carney et al. | |
| 2017/0081257 A1 | 3/2017 | Kreischer | |
| 2017/0204023 A1* | 7/2017 | Kim | C07C 2/32 |
| 2017/0341998 A1 | 11/2017 | Bischof et al. | |
| 2017/0341999 A1 | 11/2017 | Fern et al. | |
| 2017/0342000 A1 | 11/2017 | Bischof et al. | |
| 2017/0342001 A1 | 11/2017 | Fern et al. | |
| 2018/0009726 A1* | 1/2018 | Stochniol | C07C 2/26 |
| 2018/0127329 A1* | 5/2018 | Bischof | C07C 1/2076 |
| 2018/0127332 A1* | 5/2018 | Kreischer | C07C 11/02 |
| 2019/0262819 A1 | 8/2019 | Dong et al. | |
| 2019/0263729 A1* | 8/2019 | Bischof | C07C 67/297 |
| 2019/0359745 A1* | 11/2019 | Chen | C08F 10/14 |

OTHER PUBLICATIONS

Isagawa et al., "Preparation of Alcohols via Hydroalumination of Olefins," Chemical Society of Japan, Chemistry Letters, 1977, pp. 1117-1120.

Krause et al., "Aluminum Compounds, Organic," Ullmann's Encyclopedia of Indusuial Chemistry, 2012, vol. 2, pp. 585-605.

Kusumoto et al., "The Retro-Hydroformylation Reaction," Angew. Chern. Int. Ed. 2015, 54, 8458-8461.

Midland et al., "Thermal Reactions of B-Alkyl-9-borabicyclo[3.3.1]nonane (9-BBN),"f J. Am. Chem. Soc., vol. 104, Vo. 2, 1982, pp. 528-531.

Murphy et.al., "Rh-Catalyzed C—C Bond Cleavage by Transfer Hydroformylation," Science, 2015, vol. 347, Issue 6217, pp. 56-60.

Pankratyev et al., "DFT Study on Mechanism of Olefin Hydroalumination by $XA1Bu'_2$ in the Presence of $Cp_2 ZrCl_2$ Catalyst. I. Simulation of Intermediate Formation in Reaction of $HA1Bu'_2$ with $Cp_2 ZrCl_2$" Organometallics, 2009, vol. 28, No. 4, pp. 968-977.

Pappas et al., "Alkene Hydrosilylation Using Tertiary Silanes with o.-Diimine Nickel Catalysts. Redox-Active Ligands Promote a Distinct Mechanistic Pathway from Platinum Catalysts," ACS Catalysis, 2016, 6, 4105-4109.

Ruddy et al., "(N-Phosphinoamidinate)cobalt-Catalyzed Hydroboration: Alkene Isomerization Affords Terminal Selectivity," Chem. Eur. J., 2014, 20, 13 918-13 922.

Schuster et al., "Bench-Stable, Substrate-Activated Cobalt Carboxylate Pre-Catalysts for Alkene Hydrosilylation with Tertiary Silanes," ACS Catalysis, 2016, 6, 2632-2636.

Tondreau et al., "Iron Catalysts for Selective Anti-Markovnikov Alkene Hydrosilylation Using Tertiary Silanes," Science, 2012, vol. 335, pp. 567-570.

Wu et al., "Tandem Catalysis: Transforming Alcohols to Alkenes by Oxidative Dehydroxymethylation," J. Am. Chem. Soc., 2018, 140, 32, pp. 10126-10130.

* cited by examiner

US 11,498,889 B1

SELECTIVE 1-HEXENE/1-OCTENE PRODUCTION WITH 1-DECENE

FIELD OF THE INVENTION

The present disclosure relates generally to systems and methods for producing 1-decene in combination with 1-hexene, 1-octene, or both 1-hexene and 1-octene.

BACKGROUND OF THE INVENTION

The synthesis of specific carbon number normal alpha olefins—in particular, 1-hexene, 1-octene, and 1-decene—are of significant importance in the chemical industry. However, with current catalysts and reaction processes, it is difficult to selectively produce only the desired carbon number alpha olefin fraction, rather than a complex mixture of olefin products. It would be beneficial to develop new ways to produce desirable combinations of specific $C_6$-$C_{10}$ alpha olefins. Accordingly, it is to these ends that the present invention is generally directed.

SUMMARY OF THE INVENTION

This summary is provided to introduce a selection of concepts in a simplified form that are further described herein. This summary is not intended to identify required or essential features of the claimed subject matter. Nor is this summary intended to be used to limit the scope of the claimed subject matter.

A first process described herein can be used to produce 1-octene and 1-decene. This first process can comprise a) separating a composition comprising an oligomer product, the oligomer product comprising from 15 to 80 mol % $C_6$ olefins, from 20 to 80 mol % $C_8$ olefins, and from 5 to 20 mol % $C_{10}$+ olefins, into i) a first oligomer composition comprising $C_6$ alkanes and at least 85 mol % $C_6$ olefins, the $C_6$ olefins comprising at least 80 mol % 1-hexene, ii) a second oligomer composition comprising at least 85 mol % $C_8$ olefins, the $C_8$ olefins comprising at least 85 mol % 1-octene, and iii) a heavies stream comprising $C_{10}$+ olefins, b) contacting a metathesis catalyst system with all or a portion of the first oligomer composition to form a first composition comprising $C_{10}$ linear internal olefins, c) contacting the $C_{10}$ linear internal olefins (e.g., 5-decene) with an isomerization hydrofunctionalization catalyst system (such as a hydroformylation, a hydroboration, a hydrosilylation, a hydroalumination, or similar catalyst system that forms a C—X terminal bond) to form a second composition comprising a functionalized alkane, d) retro-hydrofunctionalizing the functionalized alkane (e.g., cleaving the C—X bond to form 1-decene) to form a third composition comprising 1-decene, and e) purifying the third composition to isolate a fourth composition comprising at least 90 mol % 1-decene.

A second process described herein can be used to produce 1-hexene and 1-decene. This second process can comprise a) separating a composition comprising an oligomer product, the oligomer product comprising at least 85 mol % $C_6$ olefins and at least 5 mol % $C_8$+ olefins, into i) a first oligomer composition comprising $C_6$ alkanes and at least 90 mol % $C_6$ olefins, the $C_6$ olefins comprising at least 90 mol % 1-hexene, and ii) a heavies stream comprising $C_8$+ olefins, b) contacting a metathesis catalyst system with all or a portion of the first oligomer composition to form a first composition comprising $C_{10}$ linear internal olefins, c) contacting the $C_{10}$ linear internal olefins with an isomerization hydrofunctionalization catalyst system to form a second composition comprising a functionalized alkane, d) retro-hydrofunctionalizing the functionalized alkane to form a third composition comprising 1-decene, and e) purifying the third composition to isolate a fourth composition comprising at least 90 mol % 1-decene.

Related manufacturing systems also are disclosed herein. A first (1-octene and 1-decene) manufacturing system can comprise 1) an ethylene oligomerization system configured to oligomerize ethylene in the presence of a catalyst system or catalyst system components to form a composition comprising an oligomer product, the oligomer product comprising from 20 to 80 mol % $C_6$ olefins, from 15 to 80 mol % $C_8$ olefins, and from 5 to 20 mol % $C_{10}$+ olefins, 2) a fractionation system configured to separate the composition comprising the oligomer product into i) a first oligomer composition comprising 1-hexene, ii) a second oligomer composition comprising 1-octene, and iii) a heavies stream comprising $C_{10}$+ olefins, 3) a metathesis system configured to contact a metathesis catalyst system with all or a portion of the first oligomer composition to form a first composition comprising $C_{10}$ linear internal olefins, 4) an isomerization hydrofunctionalization system configured to contact the $C_{10}$ linear internal olefins with an isomerization hydrofunctionalization catalyst system to form a second composition comprising a functionalized alkane, 5) a retro-hydrofunctionalization system configured to treat the functionalized alkane to form a third composition comprising 1-decene, and 6) a purification system configured to isolate a fourth composition comprising at least 90 mol % 1-decene from the third composition.

A second (1-hexene and 1-decene) manufacturing system can comprise 1) an ethylene oligomerization system configured to oligomerize ethylene in the presence of a catalyst system or catalyst system components to form a composition comprising an oligomer product, the oligomer product comprising at least 85 mol % $C_6$ olefins and at least 5 mol % $C_8$+ olefins, 2) a fractionation system configured to separate the composition comprising the oligomer product into a first oligomer composition comprising 1-hexene and a heavies stream comprising $C_8$+ olefins, 3) a metathesis system configured to contact a metathesis catalyst system with all or a portion of the first oligomer composition to form a first composition comprising $C_{10}$ linear internal olefins, 4) an isomerization hydrofunctionalization system configured to contact the $C_{10}$ linear internal olefins with an isomerization hydrofunctionalization catalyst system to form a second composition comprising a functionalized alkane, 5) a retro-hydrofunctionalization system configured to treat the functionalized alkane to form a third composition comprising 1-decene, and 6) a purification system configured to isolate a fourth composition comprising at least 90 mol % 1-decene from the third composition.

Both the foregoing summary and the following detailed description provide examples and are explanatory only. Accordingly, the foregoing summary and the following detailed description should not be considered to be restrictive. Further, features or variations can be provided in addition to those set forth herein. For example, certain aspects can be directed to various feature combinations and sub-combinations described in the detailed description.

BRIEF DESCRIPTION OF THE FIGURES

The following figures form part of the present specification and are included to further demonstrate certain aspects of the present invention. The invention may be better

Figure 1:
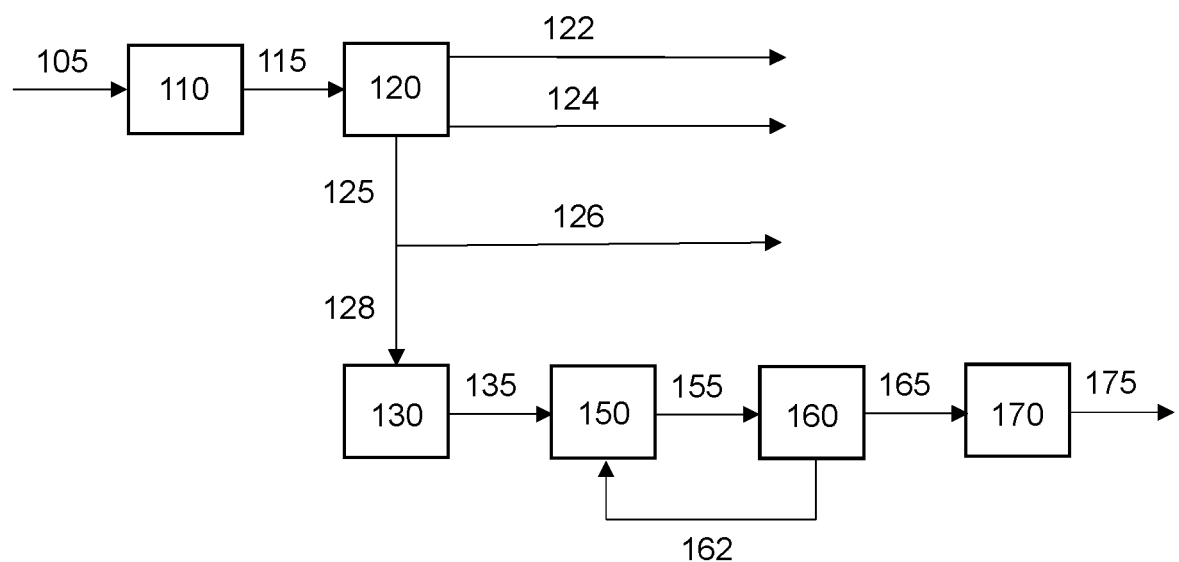
FIG. 1 illustrates a 1-octene/1-decene manufacturing system consistent with an aspect of the present disclosure.

While the inventions disclosed herein are susceptible to various modifications and alternative forms, only a few specific aspects have been shown by way of example in the drawings and described in detail below. The figures and detailed descriptions of these specific aspects are not intended to limit the breadth or scope of the inventive concepts or the appended claims in any manner. Rather, the figures and detailed descriptions are provided to illustrate the inventive concepts to a person of ordinary skill in the art and to enable such person to make and use the inventive concepts.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects, a combination of different features can be envisioned. For each and every aspect and/or feature disclosed herein, all combinations that do not detrimentally affect the designs, compositions, processes, and/or methods described herein are contemplated with or without explicit description of the particular combination. Additionally, unless explicitly recited otherwise, any aspect and/or feature disclosed herein can be combined to describe inventive features consistent with the present disclosure.

In this disclosure, while compositions, processes/methods, and systems are described in terms of "comprising" various materials, steps, and components, the compositions, processes/methods, and systems also can "consist essentially of" or "consist of" the various materials, steps, or components, unless stated otherwise.

The terms "a," "an," and "the" are intended to include plural alternatives, e.g., at least one, unless otherwise specified. For instance, the disclosure of "a $C_8$ olefin" or "an acceptor" is meant to encompass one, or combinations of more than one, $C_8$ olefin or acceptor, respectively, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; and a general reference to a butyl group includes an n-butyl group, a sec-butyl group, an iso-butyl group, and a t-butyl group.

The terms "contacting" and "combining" are used herein to describe compositions, processes/methods, and systems in which the materials are contacted or combined together in any order, in any manner, and for any length of time, unless otherwise specified. For example, the materials can be blended, mixed, slurried, dissolved, reacted, treated, impregnated, compounded, or otherwise contacted or combined in some other manner or by any suitable method or technique.

The terms "catalyst composition," "catalyst mixture," "catalyst system," and the like, do not depend upon the actual product or composition resulting from the contact or reaction of the initial components of the disclosed or claimed catalyst composition/mixture/system, the nature of the active catalytic site, or the fate of the transition metal compound, the phosphine, the heteroatomic acid or heteroatomic acid derivative, and the acceptor, after combining these components. Therefore, the terms "catalyst composition," "catalyst mixture," "catalyst system," and the like, encompass the initial starting components of the composition, as well as whatever product(s) may result from contacting these initial starting components, and this is inclusive of both heterogeneous and homogenous catalyst systems or compositions. The terms "catalyst composition," "catalyst mixture," "catalyst system," and the like, can be used interchangeably throughout this disclosure.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g., halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The term "alpha olefin" as used herein refers to any olefin that has a carbon-carbon double bond between the first and second carbon atom of the longest contiguous chain of carbon atoms. The term "alpha olefin" includes linear and branched alpha olefins and alpha olefins which can have more than one non-aromatic carbon-carbon double bond, unless expressly stated otherwise. The term "normal alpha olefin" as used herein refers to a linear aliphatic hydrocarbon mono-olefin having a carbon-carbon double bond between the first and second carbon atoms. The term "linear internal olefin" as used herein refers to a linear aliphatic hydrocarbon mono-olefin having a double bond that is not between the first and second carbon atoms.

An "aromatic compound" refers to a compound containing a cyclically conjugated moiety that follows the Hückel (4n+2) rule and containing (4n+2) pi-electrons, where n is an integer from 1 to about 5. Aromatic compounds can be monocyclic or polycyclic, unless otherwise specified. Non-limiting examples of aromatic compounds include benzene, naphthalene, and toluene, among others.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents, unless otherwise specified.

The term oligomer refers to a product that contains from 2 to 20 monomer units. The terms "oligomerization product" and "oligomer product" include all products made by the "oligomerization" process, including the "oligomers" and products which are not "oligomers" (e.g., products which contain more than 20 monomer units, or solid polymer), but exclude other non-oligomer components of an oligomerization reaction zone effluent stream, such as unreacted ethylene, organic reaction medium, and hydrogen, amongst other components.

The term "oligomerization" and its derivatives refer to processes which produce an oligomer product comprising at least 20 wt. %, 35 wt. %, 50 wt. %, or 60 wt. % products comprising from 2 to 20 monomer units. In an example, an "oligomerization" process using ethylene as the monomer produces a mixture of products comprising at least 20 wt. %, 35 wt. %, 50 wt. %, or 60 wt. % oligomers having from 4 to 40 carbon atoms.

The term "reaction zone effluent" and it derivatives (e.g., oligomerization reaction zone effluent) generally refer to all the material which exits the reaction zone through a reaction zone outlet/discharge which discharges a reaction mixture and can include reaction zone feed(s) (e.g., ethylene, catalyst system or catalyst system components, and/or solvent), and/or reaction product (e.g., oligomer product including oligomers and non-oligomers). The term "reaction zone effluent" and its derivatives can be qualified to refer to certain portions by use of additional qualifying terms. For example, while reaction zone effluent refers to all material which exits the reaction zone through the reaction zone outlet/discharge, a reaction zone oligomer product effluent refers to only the oligomer product within the reaction zone effluent.

Product compositions herein refer to the material formed from respective feedstock, e.g., a metathesis product composition contains all of the product produced from the olefin feedstock (metathesized olefin product and by-products) and excludes the feedstock olefin, solvent (if used), and catalyst system or catalyst system components; a hydroformylation product composition refers to the products produced by the hydroformylation of the olefin feedstock (aldehydes and by-products) and excludes the feedstock olefin, solvent (if used), and catalyst system or catalyst system components; a dehydroformylation product composition refers to the product produced by the dehydroformylation of the aldehydes (olefins and by-products) and excludes unconverted aldehydes, solvent (if utilized), and catalyst system and/or catalyst system components. The product composition can form part of a larger composition which can include unconverted feedstock, solvent (if utilized), and catalyst system and/or catalyst system components.

As utilized herein, the term "solvent" applies to a material which can dissolve a compound, or a material which can dilute the components of a reaction. As such, the term "solvent" can encompass materials which can act as a diluent, unless stated otherwise.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, when a chemical moiety having a certain number of carbon atoms is disclosed or claimed, the intent is to disclose or claim individually every possible number that such a range could encompass, consistent with the disclosure herein. For example, the disclosure that a moiety is a $C_1$ to $C_{18}$ hydrocarbyl group, or in alternative language, a hydrocarbyl group having from 1 to 18 carbon atoms, as used herein, refers to a moiety that can have 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ hydrocarbyl group), and also including any combination of ranges between these two numbers (for example, a $C_2$ to $C_4$ and a $C_{12}$ to $C_{16}$ hydrocarbyl group). Likewise, all other ranges disclosed herein should be interpreted in a manner similar to this example.

In general, an amount, size, formulation, parameter, range, or other quantity or characteristic is "about" or "approximate" whether or not expressly stated to be such. Whether or not modified by the term "about" or "approximately," the claims include equivalents to the quantities or characteristics.

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" or "below" any recited maximum value for the feature disclosed herein.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Disclosed herein are systems and processes for producing 1-decene in combination with 1-hexene, 1-octene, or both 1-hexene and 1-octene.

The development of processes to selectively synthesize 1-decene is uniquely challenging. The ethylene oligomerization processes that are used to generate 1-hexene and 1-octene often involve a metallocycle mechanism, which does not operate effectively for higher oligomers, such as 1-decene and above. While not wishing to be bound by theory, it is believed that intermediate chromacycles are not stable and readily fall apart before allowing insertion of the 5th ethylene to generate a 11-membered ring. Therefore, 1-decene is typically synthesized through chemical reactions and using catalyst systems that are not selective for one specific molecule (1-decene), but rather produce an array of materials that must be inefficiently separated or fractionated. The ethylene efficiency of a process to produce 1-decene would be very low, given all the other product fractions that are simultaneously being produced.

A first objective of the present invention is a system and process for producing 1-octene and 1-decene, in which an ethylene oligomerization product stream containing 1-hexene and 1-octene is separated, with the 1-octene portion being a primary product, while the 1-hexene portion is typically of lower purity (e.g., less than 95 mol %, based on $C_6$). Further, the $C_6$ fraction containing 1-hexene also contains internal and cyclic $C_6$ materials that are difficult to separate without large and complicated distillation columns and processes. Instead of purifying and cleaning up the impure $C_6$ stream, it is subjected herein to metathesis, isomerization hydrofunctionalization (e.g., hydroformylation, hydroboration, hydrosilylation, or hydroalumination, and the like), and retro-hydrofunctionalization, ultimately converting most of the 1-hexene into 1-decene, thus resulting in a selective octene/decene process.

For instance, many end-uses for 1-hexene require purities of 99 mol % or more (based on $C_6$), but as shown in the Table I for an illustrative $C_6$ fraction from an ethylene oligomerization process, it is not uncommon for the purity of 1-hexene to be ~90 mol %, and the other $C_6$ species present having boiling points within 5-15° C. of 1-hexene. From Table I, it is apparent that the boiling points of the $C_6$ species are very close, leading to complicated separations with large distillation columns in order to isolate 1-hexene at over 99 mol % purity. Beneficially, subjecting the species in Table I to metathesis would result in a far easier separation process, since only 1-hexene would metathesize to 5-decene, and the separation of alkane impurities (e.g., $C_6$ alkanes generally do not metathesize) or metathesized olefin impurities (which would not result in decene) would be significantly easier to separate from 5-decene than to separate them as the $C_6$ components that are shown in Table I.

TABLE I

| $C_6$ Species | mol % | Boiling Point (° C.) |
| --- | --- | --- |
| 1-hexene | 90.6 | 63 |
| 3-hexene | 0.2 | 66 |
| 2-hexene | 0.1 | 67 |
| n-hexane | 1.1 | 69 |
| methylcyclopentane | 4.4 | 72 |
| methylenecyclopentane | 3.7 | 76 |

Moreover, as opposed to the end-uses for 1-hexene that require purities of 99 mol % or more, most end-use applications for 1-decene only require purities of in the 95-98 mol % range (e.g., 96.5 mol % purity). This further simplifies the purification process for $C_1$'s as compared to $C_6$'s, due to the lower purity requirement of the desirable normal alpha olefin.

A second objective of the present invention is a system and process for producing 1-hexene and 1-decene, in which a selective ethylene oligomerization product stream containing 1-hexene is first produced. A portion of the 1-hexene stream is then subjected herein to metathesis, isomerization hydrofunctionalization, and retro-hydrofunctionalization, ultimately converting that portion of the 1-hexene into 1-decene, thus resulting in a selective hexene/decene process. A benefit of this hexene/decene system and process is that 1-hexene can be produced continuously, while 1-decene can be produced on demand or as-needed.

In sum, the disclosed systems and processes provide the simultaneous production of 1-decene and 1-hexene, or 1-decene and 1-octene. Advantageously, the relative amount of 1-decene produced in these systems and processes can be varied based on market demands, production capacity, and profit margins of the respective normal alpha olefin (e.g., 1-decene versus 1-hexene).

Processes to Make Octene/Decene or Hexene/Decene

Aspects of this invention are directed to processes for producing 1-decene in combination with 1-octene or 1-hexene. A first process described herein can be used to produce 1-octene and 1-decene, and the first process can comprise (or consist essentially of, or consist of) a) separating a composition comprising an oligomer product, the oligomer product comprising from 15 to 80 mol % $C_6$ olefins, from 20 to 80 mol % $C_8$ olefins, and from 5 to 20 mol % $C_{10}$+ olefins, into i) a first oligomer composition comprising $C_6$ alkanes and at least 85 mol % $C_6$ olefins, the $C_6$ olefins comprising at least 80 mol % 1-hexene, ii) a second oligomer composition comprising at least 85 mol % $C_8$ olefins, the $C_8$ olefins comprising at least 85 mol % 1-octene, and iii) a heavies stream comprising $C_{10}$+ olefins, b) contacting a metathesis catalyst system with all or a portion of the first oligomer composition to form a first composition comprising $C_{10}$ linear internal olefins, c) contacting the $C_{10}$ linear internal olefins with an isomerization hydrofunctionalization catalyst system (such as a hydroformylation, a hydroboration, a hydrosilylation, a hydroalumination, or similar catalyst system that forms a C—X terminal bond) to form a second composition comprising a functionalized alkane, d) retro-hydrofunctionalizing the functionalized alkane (e.g., cleaving the C—X bond to form 1-decene) to form a third composition comprising 1-decene, and e) purifying the third composition to isolate a fourth composition comprising at least 90 mol % 1-decene.

A second process described herein can be used to produce 1-hexene and 1-decene, and the second process can comprise (or consist essentially of, or consist of) a) separating a composition comprising an oligomer product, the oligomer product comprising at least 85 mol % $C_6$ olefins and at least 5 mol % $C_8$+ olefins, into i) a first oligomer composition comprising $C_6$ alkanes and at least 90 mol % $C_6$ olefins, the $C_6$ olefins comprising at least 90 mol % 1-hexene, and ii) a heavies stream comprising $C_8$+ olefins, b) contacting a metathesis catalyst system with all or a portion of the first oligomer composition to form a first composition comprising $C_{10}$ linear internal olefins, c) contacting the $C_{10}$ linear internal olefins with an isomerization hydrofunctionalization catalyst system to form a second composition comprising a functionalized alkane, d) retro-hydrofunctionalizing the functionalized alkane to form a third composition comprising 1-decene, and e) purifying the third composition to isolate a fourth composition comprising at least 90 mol % 1-decene.

Generally, the features of the first process and the second process (e.g., the oligomer product, the first oligomer composition, the second oligomer composition, the metathesis step, the isomerization hydrofunctionalization step, the retro-hydrofunctionalization step, and the purification step, among other features) are independently described herein and these features can be combined in any combination to further describe these two processes. Moreover, additional process steps can be performed before, during, and/or after the steps of these processes, unless stated otherwise.

Referring now to the first process, step a) separates (or fractionates) a composition comprising an oligomer product—the oligomer product comprising from 15 to 80 mol % $C_6$ olefins, from 20 to 80 mol % $C_8$ olefins, and from 5 to 20 mol % $C_{10}$+ olefins—into i) a first oligomer composition comprising $C_6$ alkanes and at least 85 mol % $C_6$ olefins, the $C_6$ olefins comprising at least 80 mol % 1-hexene, ii) a second oligomer composition comprising at least 85 mol % $C_8$ olefins, the $C_8$ olefins comprising at least 85 mol % 1-octene, and iii) a heavies stream comprising $C_{10}$+ olefins. In step a) of the first process, the composition containing the oligomer product can be a reaction zone effluent from an ethylene oligomerization reactor/system, and can be formed by contacting ethylene, a catalyst system or catalyst system components, optionally an organic reaction medium, and optionally hydrogen in a reaction zone. In an aspect, the catalyst system or the catalyst system components can comprise a heteroatomic ligand chromium compound complex and an alkylaluminum compound, or a heteroatomic ligand, a chromium compound, and an alkylaluminum compound. Hence, in addition to the oligomer product, the composition (e.g., a reaction zone effluent) can contain catalyst (activated or deactivated) and an organic reaction medium. The separating (or fractionating) of the composition containing the oligomer product can occur in one or more steps—usually, multiple steps—to form the first oligomer composition, the second oligomer composition, and the heavies stream. Representative patent documents directed to ethylene oligomerization processes and catalyst systems include U.S. Patent Publication Nos. 2017/0081257, 2017/0341998, 2017/0341999, 2017/0342000, 2017/0342001, and 2016/0375431.

As it pertains to the first process, the oligomer product in step a) contains from 15 to 80 mol % $C_6$ olefins, from 20 to 80 mol % $C_8$ olefins, and from 5 to 20 mol % $C_{10}$+ olefins prior to separating (or fractionating). For instance, the oligomer product can contain from 25 to 75 mol % $C_6$ olefins in one aspect, from 30 to 70 mol % $C_6$ olefins in another aspect, from 35 to 65 mol % $C_6$ olefins in yet another aspect, and from 40 to 60 mol % $C_6$ olefins in still another aspect. Additionally or alternatively, the oligomer product can contain from 25 to 75 mol % $C_8$ olefins in one aspect, from 30 to 70 mol % $C_8$ olefins in another aspect, from 35 to 65 mol % $C_8$ olefins in yet another aspect, and from 40 to 60 mol % $C_8$ olefins in still another aspect. Additionally or alternatively, the oligomer product can contain from 5 to 18 mol % $C_{10}$+ olefins; alternatively, from 5 to 15 mol % $C_{10}$+ olefins; alternatively, from 7 to 20 mol % $C_{10}$+ olefins; or alternatively, from 7 to 18 mol % $C_{10}$+ olefins. As one of skill in the art would readily recognize, the total of these and other components does not exceed 100 mol %.

The composition containing the oligomer product is separated into i) a first oligomer composition comprising $C_6$ alkanes and at least 85 mol % $C_6$ olefins, the $C_6$ olefins comprising at least 80 mol % 1-hexene, ii) a second oligomer composition comprising at least 85 mol % $C_8$ olefins, the $C_8$ olefins comprising at least 85 mol % 1-octene, and iii) a heavies stream comprising $C_{10}$+ olefins. Referring now to the first oligomer composition which, in some aspects, can contain at least 85 mol %, at least 90 mol %, at least 93 mol %, or at least 95 mol % $C_6$ olefins. Therefore, typical ranges for the amount of $C_6$ olefins in the first composition can include, but are not limited to, from 85 to 99 mol %, from 90 to 99.5 mol %, from 93 to 98 mol %, from 95 to 99 mol %, and the like. At least 80 mol % of the $C_6$ olefins is 1-hexene, but more often, the $C_6$ olefins contain at least 85 mol %, at least 90 mol %, or at least 95 mol % 1-hexene; therefore, typical ranges include from 80 mol % to 98 mol %, from 80 mol % to 95 mol %, from 85 mol % to 95 mol %, or from 90 to 99 mol % 1-hexene. In addition to 1-hexene, the $C_6$ olefins can contain internal and cyclic $C_6$ olefins (e.g., 2-hexene, 3-hexene, methylenecyclopentane, etc.), and the $C_6$ olefins often can contain from 0.1 to 10 mol %, from 0.5 to 8 mol %, from 0.5 to 6 mol %, from 1 to 8 mol %, or from 1 to 6 mol % of a total of internal and cyclic $C_6$ olefins. $C_6$ alkanes also are present in the first composition; representative $C_6$ alkanes include methylcyclopentane and n-hexane. Generally, the first composition contains from 0.5 to 12 mol %, from 0.5 to 10 mol %, from 1 to 10 mol %, from 1 to 8 mol %, from 1.5 to 8 mol %, from 2 to 8 mol %, or from 2 to 6 mol %, $C_6$ alkanes.

In the first process, the second oligomer composition can comprise at least 85 mol % $C_8$ olefins, and the $C_8$ olefins can contain at least 85 mol % 1-octene. In some aspects, the second oligomer composition can contain at least 90 mol %, at least 95 mol %, at least 96 mol %, or at least 97 mol % $C_8$ olefins. Therefore, typical ranges for the amount of $C_8$ olefins in the second composition can include, but are not limited to, from 85 to 99 mol %, from 90 to 99.5 mol %, from 95 to 99.5 mol %, from 97 to 99 mol %, and the like. At least 85 mol % of the $C_8$ olefins is 1-octene, but more often, the $C_8$ olefins contain at least 90 mol %, at least 95 mol %, or at least 97 mol % 1-octene; therefore, typical ranges include from 85 mol % to 98 mol %, from 90 mol % to 99 mol %, from 95 mol % to 98 mol %, or from 97 to 99.5 mol % 1-octene.

Referring now to step b) of the first process, a metathesis catalyst system is contacted with all or a portion of the first oligomer composition to form a first composition comprising $C_{10}$ linear internal olefins. The first composition typically can comprise at least 85 mol %, at least 90 mol %, at least 92 mol %, or at least 95 mol % $C_{10}$ linear internal olefins, based on $C_6$+ olefins in the first composition. Suitable metathesis catalyst systems for step b) are disclosed hereinbelow, and any suitable conditions for the metathesis step b) can be employed, as would be recognized by those skilled in the art in view of this disclosure, and for example, U.S. Pat. No. 8,765,984.

Optionally, prior to step c), the first process can further comprise a step of isolating a composition comprising at least 90 mol %, at least 93 mol %, or at least 96 mol % $C_{10}$ linear internal olefins from the first composition. Any suitable technique can be used, such as extraction, filtration, evaporation, distillation, and the like, as well as any combination thereof. Beneficially, $C_6$ alkanes in the first composition do not metathesize, so these materials will be relatively easy to separate from $C_{10}$ linear internal olefins. Likewise, methylenecyclopentane is unreactive in metathesis, so this material also will be relatively easy to separate from $C_{10}$ linear internal olefins. Further, internal $C_6$ olefins metathesize to form non-$C_{10}$ olefins, which also become easier to separate from $C_{10}$ linear internal olefins.

In step c), the $C_{10}$ linear internal olefins (e.g., 5-decene) are contacted with an isomerization hydrofunctionalization catalyst system to form a second composition comprising a functionalized alkane. Any suitable isomerization hydrofunctionalization catalyst system can be used, provided that it is suitable for chain-walking the double bond to the terminal position and then inducing a terminal double bond functionalization reaction. Illustrative catalyst systems include hydroformylation catalyst systems, hydroboration catalyst systems, hydrosilylation catalyst systems, hydroalumination catalyst systems, and the like; a functionalized alkane with a C—X terminal bond is formed.

In one aspect, the isomerization hydrofunctionalization catalyst system in step c) can be a hydroformylation catalyst system, and the functionalized alkane is a $C_{11}$ aldehyde (for the C—X terminal bond, X is a formyl group). Thus, in step c), the $C_{10}$ linear internal olefins can be contacted with a hydroformylation catalyst system, carbon monoxide, and hydrogen to form a second composition comprising $C_{11}$ aldehydes. Consistent with a further aspect of this invention, step c) can comprise contacting the linear internal olefins with a hydroformylation catalyst system and syngas (also referred to as synthesis gas) to form the aldehydes. As would be recognized by those skilled in the art, syngas is a mixture containing predominately carbon monoxide and hydrogen. Syngas also can contain carbon dioxide and methane in lesser amounts.

If used as the isomerization hydrofunctionalization catalyst system, the hydroformylation catalyst system can be used with carbon monoxide and hydrogen to form $C_{11}$ aldehydes from $C_{10}$ linear internal olefins. Any suitable conditions for the hydroformylation in step c) can be employed, as would be recognized by those skilled in the art in view of this disclosure. Any suitable hydroformylation catalyst system can be used in the hydroformylation step, non-limiting examples of which can include a rhodium compound, a cobalt compound, a ruthenium compound, an iridium compound, a platinum compound, a palladium compound, an iron compound, or any combination thereof. For instance, the hydroformylation catalyst system can comprise a rhodium compound; alternatively, a cobalt compound; alternatively, a ruthenium compound; alternatively, an iridium compound; alternatively, a platinum compound; alternatively, a palladium compound; or alternatively, an iron compound.

Typically, using hydroformylation in step c) produces both linear and branched $C_{11}$ aldehydes—but, primarily linear aldehydes—and some hydrogenated olefin. For instance, the $C_{11}$ aldehydes can contain at least 80 mol %, at least 85 mol %, at least 90 mol %, or at least 95 mol % $C_{11}$ linear aldehydes. Branched aldehydes are typically minimized, since they may produce internal decenes in the subsequent retro-hydrofunctionalization (e.g., dehydroformylation) step.

Optionally, prior to step d), the first process can further comprise a step of isolating a composition comprising at least 90 mol %, at least 93 mol %, or at least 96 mol % $C_{11}$ aldehydes from the second composition. As above, any suitable technique can be employed, such as extraction, filtration, evaporation, distillation, and the like, as well as any combination thereof. Generally, the aldehydes will be separated from unreacted or residual olefins and from decane, which can be a by-product of the hydroformylation reaction.

In other aspects of step c), the $C_{10}$ linear internal olefins (e.g., 5-decene) are contacted with an isomerization hydrofunctionalization catalyst system to form a second composition comprising a functionalized alkane, and the isomerization hydrofunctionalization catalyst system is a hydroboration catalyst system, a hydrosilylation catalyst system, or a hydroalumination catalyst system. As an example, the isomerization hydrofunctionalization catalyst system in step c) can be a hydroboration catalyst system, and the functionalized alkane is a $C_{10}$ alkylboron (for the C—X terminal bond, X is boron). Thus, in step c), the $C_{10}$ linear internal olefins can be contacted with a hydroboration catalyst system to form a second composition containing a functionalized alkane. A representative example of a suitable hydroboration catalyst system is disclosed in U.S. Pat. No. 9,120,826, which describes the hydroboration of a linear internal olefin (the example section demonstrates 4-octene) to form a terminal alkylboron compound, followed by a dehydroboration treatment step (e.g., thermal treatment) to cleave the boron-carbon bond and form a linear terminal olefin.

As would be recognized by a skilled artisan, any suitable hydroboration, hydrosilylation, and hydroalumination techniques and catalyst systems can be used herein, and representative references directed to such subject matter include Chem. Eur. J. 2014, 20, 13918-13922; J. Am. Chem. Soc. 1982, 104, 528-531; Accounts of Chemical Research, 864-874, 2012, Vol. 45, No. 6; ACS Catal. 2016, 6, 4105-4109; ACS Catal. 2016, 6, 2632-2636; Science, 3 Feb. 2012, Vol. 335, 567-570; Chemistry Letters, 1977, 1117-1120; Organometallics 2009, Vol. 28, No. 4, 968-977; and Ullmann's Encyclopedia of Industrial Chemistry, 2012, Vol. 2, Aluminum Compounds, Organic, 585-605.

In step d), the functionalized alkane can be retro-hydrofunctionalized (e.g., cleaving the C—X bond) to form a third composition comprising 1-decene. Any suitable retro-hydrofunctionalization technique, such as thermal treatment, that that cleaves the C—X bond to form 1-decene can be used (and the functionalization agent from step c) also can be formed in addition to 1-decene).

In one aspect, hydroformylation is used in step c) and the resulting $C_{11}$ aldehydes are contacted with a dehydroformylation catalyst system in step d). While not limited thereto, this retro-hydrofunctionalization step uses a catalyst system (a dehydroformylation catalyst system) that can comprise i) a transition metal compound, a phosphine, and a heteroatomic acid or heteroatomic acid derivative, or ii) a phosphine transition metal compound complex and a heteroatomic acid or heteroatomic acid derivative, to form a third composition comprising 1-decene. Suitable dehydroformylation catalyst systems for step d) are disclosed hereinbelow, and any suitable conditions for the dehydroformylation step d) can be employed, as would be recognized by those skilled in the art in view of this disclosure and representative patent documents, such as U.S. Pat. Nos. 10,723,672, 10,435,334, and 10,183,899, and U.S. Patent Publication No. 2019/0262819. Moreover, other suitable retro-hydrofunctionalization (or dehydroformylation) catalyst systems are disclosed in Kusumoto, Tatsuki, and Nozaki, Angew. Chem. Int. Ed., 2015, 54, 8458-8461 (e.g., Catalyst F and Entry 7, and others from Table 1 on page 8459).

The amount of the transition metal in the dehydroformylation catalyst system relative to the amount of aldehyde is not particularly limited. For instance, the minimum molar ratio of the Cn aldehyde to the transition metal (of the transition metal compound or the phosphine transition metal compound complex) can be 1:1, 2:1, 5:1, or 10:1; additionally or alternatively, the maximum molar ratio of the $C_{11}$ aldehyde to the transition metal can be 10,000:1, 1000:1, 500:1, or 250:1. In an aspect, the $C_{11}$ aldehyde to transition metal (of the transition metal compound or the phosphine transition metal compound complex) molar ratio can be in a range from any minimum molar ratio disclosed herein to any maximum molar ratio disclosed herein. In some non-limiting aspects, the molar ratio can be in a range from 1:1 to 10,000:1, from 2:1 to 1000:1, from 5:1 to 500:1, or from 10:1 to 250:1. As those skilled in the art would readily recognize, the $C_{11}$ aldehyde to transition metal molar ratio can change as the dehydroformylation reaction proceeds. Accordingly, these ranges of molar ratios are meant to encompass the initial ratio as well as any molar ratio of $C_{11}$ aldehyde to transition metal encountered as the dehydroformylation reaction proceeds.

When used in the catalyst system, the amount of the acceptor is not particularly limited. For instance, a minimum acceptor to $C_{11}$ aldehyde molar ratio of 0.2:1, 0.5:1, 0.75:1, 1:1, 1.5:1, or 2:1 can be used; or additionally or alternatively, a maximum acceptor to $C_{11}$ aldehyde molar ratio of 1000:1, 500:1, 100:1, 50:1, 25:1, 10:1, or 5:1 can be used. In an aspect, the acceptor to $C_{11}$ aldehyde molar ratio can be in a range from any minimum molar ratio disclosed herein to any maximum molar ratio disclosed herein. In some non-limiting aspects, the molar ratio can be in a range from 0.2:1 to 1000:1, from 0.5:1 to 500:1, from 0.75:1 to 100:1, from 1:1 to 10:1, or from 0.5:1 to 5:1. As those skilled in the art would readily recognize, the acceptor to $C_{11}$ aldehyde molar ratio can change as the dehydroformylation reaction proceeds. Accordingly, these ranges of molar ratios are meant to encompass the initial reactant ratio as well as any molar ratio of the acceptor to $C_{11}$ aldehyde encountered as the dehydroformylation reaction proceeds.

Step d) can be conducted any suitable temperature. For instance, step d) can be conducted at a minimum temperature of 0° C., 10° C., 15° C., or 20° C.; additionally or alternatively, at a maximum temperature of 150° C., 125° C., 100° C., or 75° C. In an aspect, the step d) can be conducted in a range from any minimum temperature disclosed herein to any maximum temperature disclosed herein. In some non-limiting aspects, the temperature can be in a range from 0° C. to 150° C.; alternatively, from 0° C. to 100° C.; alternatively, from 10° C. to 125° C.; alternatively, from 10° C. to 75° C.; alternatively, from 15° C. to 150° C.; alternatively, from 15° C. to 100° C.; alternatively, from 20° C. to 125° C.; or alternatively, from 20° C. to 75° C. These temperature ranges also are meant to encompass circumstances where step d) is conducted at a series of different temperatures, instead of at a single fixed temperature, falling within the respective temperature ranges.

Generally, step d) can be conducted at any suitable pressure, and this can vary depending upon the particular acceptor that is used (e.g., to maintain the acceptor in the liquid phase). While not being limited thereto, step d) can be conducted at a reaction pressure in a range from 0 to 2000 psig (0 to 13,785 kPa), from 10 to 2000 psig (69 to 13,785 kPa), from 0 to 1000 psig (0 to 6,890 kPa), from 5 to 1000 psig (34 to 6,890 kPa), from 5 to 750 psig (34 to 5,170 kPa), from 5 to 500 psig (34 to 3,450 kPa), from 5 to 250 psig (34 to 1,720 kPa), from 5 to 150 psig (34 to 1,030 kPa), or from 10 to 100 psig (69 to 689 kPa). In some aspects, step d) can be conducted at atmospheric pressure, while in other aspects, step d) can be conducted at sub-atmospheric pressures. These pressure ranges also are meant to encompass circumstances where step d) is conducted at a series of different pressures, instead of at a single fixed pressure, falling within the respective pressure ranges.

Step d) can be conducted in any suitable reactor or vessel in order to form 1-decene, non-limiting examples of which can include a fixed bed reactor, a stirred tank reactor, a plug flow reactor, a loop reactor, and a tubular reactor, including more than one reactor in series or in parallel, and including any combination of reactor types and arrangements. Step d) can be a batch process in some aspects, while in other aspects, step d) can be a continuous process.

In particular aspects of this invention, the aldehydes and the catalyst composition can be contacted in the absence of a solvent. However, in other aspects, the aldehydes and the catalyst composition can be contacted in the presence of a solvent. Typically, when used, the solvent can be present in an amount up to 1,000 wt. %, based on the weight of the aldehydes. Alternatively, the aldehydes and the catalyst system can be contacted in the presence of a solvent in an amount up 750 wt. %, up to 500 wt. %, up to 250 wt. %, up to 200 wt. %, up to 150 wt. %, or up to 100 wt. %. When a solvent is utilized, the minimum amount of solvent utilized can be at least 5 wt. %, at least 10 wt. %, at least 25 wt. %, at least 50 wt. %, or at least 75 wt. %, based on the weight of the aldehydes. Generally, the amount of solvent which can be utilized can range from any minimum amount of solvent disclosed herein to any maximum amount of solvent disclosed herein. In some non-limiting aspects, the aldehydes and the catalyst system can be contacted in the presence of a solvent in an amount of from 5 wt. % to 1,000 wt. %, from 10 wt. % to 750 wt. %, from 25 wt. % to 500 wt. %, from 50 wt. % to 250 wt. %, from 50 wt. % to 150 wt. %, or from 75 wt. % to 125 wt. %, based on the weight of the aldehydes.

As described herein, step d) can be conducted in the presence of a solvent. In one aspect, the solvent can comprise, consist essentially of, or consist of, a polar solvent, while in another aspect, the solvent can comprise, consist essentially of, or consist of, a hydrocarbon, a ketone, an alcohol, an ether, or any combination thereof. Hence, mixtures and/or combinations of solvents can be utilized in the normal alpha olefin synthesis processes disclosed herein.

In an aspect, the solvent can comprise, consist essentially of, or consist of, a hydrocarbon solvent. Suitable hydrocarbon solvents can include, for example, aliphatic hydrocarbons (e.g., pentane, hexane, heptane, octane, decane, and combinations thereof) and aromatic hydrocarbons (e.g., benzene, toluene, xylene(s), ethylbenzene, and combinations thereof).

In an aspect, the solvent can comprise, consist essentially of, or consist of, a ketone, an ether, or any combination thereof; alternatively, a ketone; or alternatively, an ether. Suitable ketones or ethers include $C_2$ to $C_{20}$ ketones or ethers; alternatively, $C_2$ to $C_{10}$ ketones or ethers; or alternatively, $C_2$ to $C_5$ ketones or ethers. Non-limiting examples of suitable ketone solvents can include acetone, ethyl methyl ketone, or any combination thereof. Suitable ether solvents can be cyclic or acyclic, non-limiting examples of which can include dimethyl ether, diethyl ether, methyl ethyl ether, dibutylether, monoethers or diethers of glycols (e.g., a dimethyl glycol ether), glyme, diglyme, tetraglyme, furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an aspect, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group.

Generally, a molar yield of 1-decene in step d) can be at least 20%, at least 30%, at least 40%, at least 50%, at least 75%, or at least 90%. This molar yield of 1-decene is based on the initial amount of $C_{11}$ aldehydes in step d).

In aspects of this invention in which the dehydroformylation catalyst system does not contain an acceptor, all or a portion of the carbon monoxide and hydrogen formed in step d) can be recycled and used in step c).

In step e) of the first process, the third composition—comprising 1-decene—can be purified to isolate a fourth composition containing at least 90 mol % 1-decene. The fourth composition containing 1-decene can be isolated or separated from the third composition using any suitable technique, such as extraction, filtration, evaporation, distillation, or any combination of two or more of these techniques. While the fourth composition contains at least 90 mol % 1-decene, in some aspects, the fourth composition can contain at least 92 mol %, at least 95 mol %, at least 97 mol %, or at least 98 mol % 1-decene. Therefore, typical ranges for the amount of 1-decene in the fourth composition can include, but are not limited to, from 90 to 99 mol %, from 92 to 99.5 mol %, from 95 to 99 mol %, from 98 to 99.5 mol %, and the like.

Optionally, the first process can further comprise a step of contacting the metathesis catalyst system with all or a portion of the $C_8$ olefin composition to form a $C_{14}$ olefin composition. Also optionally, the first process can further comprise a step of contacting the metathesis catalyst with a light oligomer composition comprising $C_6$ and $C_8$ olefins, to form a composition comprising $C_{10}$-$C_{14}$ linear internal olefins. The light oligomer composition can be formed by combining, in any relative amounts, at least a portion of the first oligomer composition (containing 1-hexene) and the second oligomer composition (containing 1-octene).

Referring now to the second process, step a) separates (or fractionates) a composition comprising an oligomer product—the oligomer product comprising at least 85 mol % $C_6$ olefins and at least 5 mol % $C_8$+ olefins—into i) a first oligomer composition comprising $C_6$ alkanes and at least 90 mol % $C_6$ olefins, the $C_6$ olefins comprising at least 90 mol % 1-hexene, and ii) a heavies stream comprising $C_8$+ olefins. As with the first process, in step a) of the second process, the composition containing the oligomer product can be a reaction zone effluent from an ethylene oligomerization reactor/system. In addition to the oligomer product, the composition (e.g., a reaction zone effluent) can contain catalyst (activated or deactivated) and an organic reaction medium. The separating (or fractionating) of the composition containing the oligomer product can occur in one or more steps—usually, multiple steps—to form the first oligomer composition and the heavies stream.

It is important to note that the oligomer product in the second process is different from the oligomer product in the first process, and the resulting fractionated compositions also are different. In the first process, the oligomer product comprises from 15 to 80 mol % $C_6$ olefins, from 20 to 80 mol % $C_8$ olefins, and from 5 to 20 mol % $C_{10}$+ olefin, while the oligomer product in the second process comprises at least 85 mol % $C_6$ olefins and at least 5 mol % $C_8$+ olefins. In the first process, the oligomer product is separated into a first oligomer composition (predominantly $C_6$), a second oligomer composition (predominantly $C_8$), and a heavies stream comprising $C_{10}$+ olefins, whereas the oligomer product in the second process is separated into a first oligomer composition (predominantly $C_6$) and a heavies stream comprising $C_8$+ olefins. The composition containing the oligomer product from the second process often can be result from a 1-hexene process, whereas the composition containing the oligomer product from the first process can result from a 1-hexene/1-octene process.

As it pertains to the second process, the oligomer product in step a) contains at least 85 mol % $C_6$ olefins and at least 5 mol % $C_8$+ olefins prior to separating (or fractionating). For instance, the oligomer product can contain at least 87 mol % $C_6$ olefins in one aspect, at least 90 mol % $C_6$ olefins in another aspect, at least 91 mol % $C_6$ olefins in yet another aspect, and at least 93 mol % $C_6$ olefins in still another aspect. Additionally or alternatively, the oligomer product can contain from 5 to 15 mol % $C_8$+ olefins; alternatively, from 5 to 12 mol % $C_8$+ olefins; alternatively, from 6 to 14 mol % $C_8$+ olefins; or alternatively, from 7 to 13 mol % $C_8$+ olefins. As one of skill in the art would readily recognize, the total of these and other components does not exceed 100 mol %.

The composition containing the oligomer product is separated into i) a first oligomer composition comprising $C_6$ alkanes and at least 90 mol % $C_6$ olefins, the $C_6$ olefins comprising at least 90 mol % 1-hexene, and ii) a heavies stream comprising $C_8$+ olefins. Referring now to the first oligomer composition which, in some aspects, can contain at least 92 mol %, at least 94 mol %, at least 96 mol %, or at least 98 mol % $C_6$ olefins. Therefore, typical ranges for the amount of $C_6$ olefins in the first composition can include, but are not limited to, from 92 to 99 mol %, from 94 to 99.9 mol %, from 96 to 99.9 mol %, from 98 to 99.9 mol %, and the like. At least 90 mol % of the $C_6$ olefins is 1-hexene, but more often, the $C_6$ olefins contain at least 94 mol %, at least 96 mol %, or at least 98 mol % 1-hexene; therefore, typical ranges include from 90 mol % to 99 mol %, from 94 mol % to 99.9 mol %, from 96 mol % to 99.9 mol %, or from 98 to 99.9 mol % 1-hexene. In addition to 1-hexene, the $C_6$ olefins can contain often minimal amounts of internal and cyclic $C_6$ olefins (e.g., 2-hexene, 3-hexene, methylenecyclopentane, etc.), and the $C_6$ olefins often can contain from 0.1 mol % to 3 mol %, from 0.2 mol % to 2 mol %, or from 0.25 mol % to 1 mol %, of a total of internal and cyclic $C_6$ olefins. $C_6$ alkanes also are present in the first composition at often minimal amounts; representative $C_6$ alkanes include methylcyclopentane and n-hexane. Generally, the first composition in the second process contains from 0.1 mol % to 1.5 mol %, from 0.15 mol % to 1 mol %, or from 0.2 mol % to 0.75 mol %, $C_6$ alkanes.

Step b), step c), step d), and step e) of the second process can be performed generally as described herein for the respective step b), step c), step d), and step e) of the first process.

Optionally, similar to the first process, the second process—prior to step c)—can further comprise a step of isolating a composition comprising at least 90 mol %, at least 93 mol %, or at least 96 mol % $C_{10}$ linear internal olefins from the first composition. Any suitable technique can be used, such as extraction, filtration, evaporation, distillation, and the like, as well as any combination thereof. Beneficially, $C_6$ alkanes in the first composition do not metathesize, so these materials will be relatively easy to separate from $C_{10}$ linear internal olefins. Likewise, methylenecyclopentane is unreactive in metathesis, so this material also will be relatively easy to separate from $C_{10}$ linear internal olefins. Further, internal $C_6$ olefins metathesize to form non-$C_{10}$ olefins, which also become easier to separate from $C_{10}$ linear internal olefins.

Optionally, similar to the first process, the second process—prior to step d)—can further comprise a step of isolating a composition comprising at least 90 mol %, at least 93 mol %, or at least 96 mol % $C_{11}$ aldehydes from the second composition. As above, any suitable technique can be employed, such as extraction, filtration, evaporation, distillation, and the like, as well as any combination thereof. Generally, the aldehydes will be separated from unreacted or residual olefins and from decane, which can be a by-product of the hydroformylation reaction.

Metathesis Catalyst Systems

While not limited thereto, the metathesis catalyst systems disclosed herein can be used to convert 1-hexene in the first oligomer composition to form a first composition containing $C_{10}$ linear internal olefins. Any suitable metathesis catalyst system can be used in the metathesis step, non-limiting examples of which can include a metal oxide based metathesis catalyst system, a metal halide based metathesis catalyst system, a metal carbene based metathesis catalyst system, or any combination thereof. In one aspect, the metathesis catalyst system can be a metal oxide based metathesis catalyst system or a metal halide based metathesis catalyst system, while in another aspect, the metathesis system catalyst can be a metal oxide based metathesis catalyst system; alternatively, a metal halide based metathesis catalyst system; or alternatively, a metal carbene based metathesis catalyst system.

Metal oxide based metathesis catalyst systems can comprise (or consist essentially of, or consist of) cobalt oxide, molybdenum oxide, tungsten oxide, rhenium oxide, or any combination thereof. For instance, the metal oxide based catalyst system can comprise (or consist essentially of, or consist of) cobalt oxide; alternatively, molybdenum oxide; alternatively, tungsten oxide; or alternatively, rhenium oxide. Optionally, the metal oxide based metathesis catalyst system can further comprise a support, or a metal alkyl activator, or both a support and a metal alkyl activator. Illustrative supports can include alumina, silica, silica-alumina, and aluminum-phosphate, amongst other solid oxide materials. Accordingly, non-limiting examples of supported metal oxide based metathesis catalyst systems can include molybdenum oxide on alumina ($MoO_3/Al_2O_3$), tungsten oxide on silica ($WO_3/SiO_2$), rhenium oxide on alumina ($Re_2O_7/Al_2O_3$), cobalt oxide and molybdenum oxide on alumina ($CoO/MoO_3/Al_2O_3$), and rhenium oxide on alumina activated with tetramethyl tin ($Re_2O_7/Al_2O_3/SnMe_4$). Other suitable metal oxide based metathesis catalyst systems are known to those skilled in the art.

Further, the metal oxide based metathesis catalyst system can include a metal alkyl activator, which can include alkyl lithium, alkyl magnesium, alkyl aluminum, alkyl tin compounds, or any mixture thereof. In an aspect, the metal alkyl activator can be an alkyl lithium compound. In another aspect, the metal alkyl activator can be an alkyl magnesium compound. In another aspect, the metal alkyl activator can be an alkyl aluminum compound. In yet another aspect, the metal alkyl activator can be an alkyl tin compound. Non-limiting examples of alkyl aluminum compounds can include trialkyl aluminum compounds and/or alkyl aluminum halide compounds. The alkyl groups on the metal alkyl activator can include any $C_1$ to $C_{10}$ hydrocarbyl group, or alternatively, any $C_1$ to $C_5$ hydrocarbyl group. In various aspects, the alkyl group for the metal alkyl activator can be a methyl group, ethyl group, n-propyl group, iso-propyl group, n-butyl group, sec-butyl group, or tert-butyl group; alternatively, a methyl group, ethyl group, n-butyl group, sec-butyl group, or tert-butyl group; alternatively, a methyl group; alternatively, an ethyl group; alternatively, an n-butyl group; alternatively, a sec-butyl group; or alternatively, a tert-butyl group. Representative examples of suitable trialkyl aluminum compounds can include trimethylaluminum, triethylaluminum, and triisobutylaluminum. The halide of the alkyl aluminum halide compound can be chloride, bromide, or iodide; alternatively, chloride; alternatively, bromide; or alternatively, iodide. Examples of suitable alkyl aluminum halide compounds can include ethylaluminum dichloride, diethylaluminum chloride, and ethylaluminum sesquichloride. Suitable and non-limiting examples of alkyl tin compounds can include tetramethyl tin, tetraethyl tin, and tetrabutyl tin.

Metal halide based metathesis catalyst systems can comprise (or consist essentially of, or consist of) a halide of tungsten, a halide of molybdenum, or a combination thereof. For instance, the metal halide based metathesis catalyst system can comprise (or consist essentially of, or consist of) a halide of tungsten, or alternatively, a halide of molybdenum. The halide of the metal halide based metathesis catalyst system can be chloride, bromide, or iodide. In one aspect, the halide can be chloride, and in another aspect, the halide can be bromide, and in yet another aspect, the halide can be iodide. Hence, the metal halide based metathesis catalyst system can comprise (or consist essentially of, or consist of) tungsten chloride, molybdenum chloride, or a mixture thereof; alternatively, tungsten chloride; or alternatively, molybdenum chloride.

Optionally, the metal halide based metathesis catalyst system can further comprise a metal alkyl activator (as described herein), oxygen, an alcohol, or any combination thereof; alternatively, a metal alkyl activator; alternatively, oxygen; or alternatively, an alcohol. Non-limiting examples of metal halide based metathesis catalyst systems can include tungsten chloride/tetrabutyl tin ($WCl_6/SnMe_4$), tungsten chloride/ethylaluminum dichloride ($WCl_6/EtAlCl_2$), tungsten chloride/ethyl-aluminum dichloride/ethyl alcohol ($WCl_6/EtAlCl_2/EtOH$), molybdenum chloride/triethyl aluminum ($MoCl_5/AlEt_3$), and molybdenum chloride/triethyl aluminum/$O_2$ ($MoCl_5/AlEt_3/O_2$). Other suitable metal halide based metathesis catalyst systems are known to those skilled in the art.

Metal carbene based metathesis catalyst systems can comprise (or consist essentially of, or consist of) tungsten, tantalum, osmium, molybdenum, ruthenium, or any combination thereof. For instance, the metal carbene based metathesis catalyst system can comprise (or consist essentially of, or consist of) tungsten; alternatively, tantalum; alternatively, osmium; alternatively, molybdenum; or alternatively, ruthenium. These metal carbene based metathesis catalyst systems can contain compounds which have a stable metal-carbon double bond or can form a metal-carbon double bond in situ from a metal precursor having a stable metal-carbon single bond.

In an aspect, a ruthenium carbene based metathesis catalyst system can comprise a compound having the structure $L^1L^2X_2Ru=CHR^1$, wherein $L^1$ and $L^2$ can be an organic ligand, X can be a halide, and $R^1$ can be hydrogen or a hydrocarbyl group. Generally, the compound in the ruthenium carbene based metathesis catalyst system having the structure $L^1L^2X_2Ru=CHR^1$ can be described using any combination of $L^1$, $L^2$, X, or $R^1$ described herein.

Generally, $L^1$ and $L^2$ independently can be $R'_3P$, an imidazolinylidene group, or an imidazolidinylidene group. In some aspects, $L^1$ and $L^2$ can be $R'_3P$; alternatively, $L^1$ can be $R'_3P$ and $L^2$ can be an imidazolinylidene group or an imidazolidinylidene group; alternatively, $L^1$ can be $R'_3P$ and $L^2$ can be an imidazolinylidene group; alternatively, $L^1$ can be $R'_3P$ and $L^2$ can be an imidazolidinylidene group; alternatively, $L^1$ and $L^2$ can be imidazolinylidene groups; or alternatively, $L^1$ and $L^2$ can be imidazolidinylidene groups. In aspects of this invention, R' can be a hydrocarbyl group, where each R' of $R'_3P$ can be the same; alternatively, each R' of $R'_3P$ can be different; or alternatively, one R' of $R'_3P$ can be different from the other two R' groups. In some aspects, each R' of $R'_3P$ independently can be a $C_1$ to $C_{15}$ hydrocarbyl group; or alternatively, a $C_1$ to $C_{10}$ hydrocarbyl group. In other aspects, each hydrocarbyl R' of $R'_3P$ independently can be an alkyl group or an aromatic group; alternatively, an alkyl group; or alternatively, an aromatic group. In an aspect, each alkyl R' of $R'_3P$ independently can be a methyl group, ethyl group, n-propyl group, isopropyl group, tert-butyl group, neo-pentyl group, cyclopentyl group, or cyclohexyl group. In some aspects, one or more R' groups of $R'_3P$ can be a phenyl group, or alternatively, a substituted phenyl group. In an aspect, the substituents of any substituted phenyl group independently can be a $C_1$-$C_5$ organyl group, or alternatively, a $C_1$-$C_5$ hydrocarbyl group. In some aspects, $R'_3P$ can be a trialkyl phosphine or triphenyl phosphine; alternatively, a trialkyl phosphine; or alternatively, triphenyl phosphine. In an aspect, $R'_3P$ can be trimethyl phosphine, triethyl phosphine, triisopropyl phosphine, tri-tert-butyl phosphine, tri-neopentyl phosphine, tricyclopentyl phosphine, tricyclohexyl phosphine, or triphenyl phosphine; alternatively, triisopropyl phosphine, tri-tert-butyl phosphine, tri-neopentyl phosphine, tricyclopentyl phosphine, tricyclohexyl phosphine, or triphenyl phosphine; alternatively, tricyclopentyl phosphine, tricyclohexyl phosphine, or triphenyl phosphine; alternatively, tricyclopentyl phosphine or tricyclohexyl phosphine; alternatively, tricyclopentyl phosphine; alternatively, tricyclohexyl phosphine; or alternatively triphenyl phosphine.

In an aspect, the imidazolinylidene group or imidazolidinylidene group can be a $C_3$ to $C_{80}$ imidazolinylidene group or imidazolidinylidene group; alternatively, a $C_3$ to $C_{50}$ imidazolinylidene group or imidazolidinylidene group; or alternatively, a $C_5$ to $C_{40}$ imidazolinylidene group or imidazolidinylidene group. In some aspects, the imidazolinylidene group can be a 1,3-disubstituted imidazolinylidene group. In some aspects, the imidazolidinylidene group can be a 1,3-disubstituted imidazolidinylidene group. In an aspect, the 1,3-substituents of the 1,3-disubstituted imidazolinylidene group or 1,3-disubstituted imidazolidinylidene group independently can be any suitable hydrocarbyl group. In an aspect, the 1,3-substituents of the 1,3-disubstituted imidazolinylidene group or 1,3-disubstituted imidazolidinylidene group independently can be a $C_1$ to $C_{30}$ hydrocarbyl group. In some aspects, the 1,3-substituents of the 1,3-disubstituted imidazolinylidene group or 1,3-disubstituted imidazolidinylidene group independently can be a $C_6$ to $C_{20}$ aromatic group or a $C_1$ to $C_{10}$ alkyl group. In other aspects, the 1,3-substituents of the 1,3-disubstituted imidazolinylidene group or 1,3-disubstituted imidazolidinylidene group independently can be a $C_6$ to $C_{20}$ aromatic group, or alternatively, a $C_1$ to $C_{10}$ alkyl group. In an aspect, each aromatic group of the 1,3-disubstituted imidazolinylidene group or 1,3-disubstituted imidazolidinylidene group independently can be a substituted aromatic group. In some aspects, the substituted aromatic group of the 1,3-disubstituted imidazolinylidene group or 1,3-disubstituted imidazolidinylidene group can be a 2-disubstituted phenyl group, a 2,6-disubstituted phenyl group, or a 2,4,6-trisubstituted phenyl group; alternatively, a 2,6-disubstituted phenyl group; or alternatively, a 2,4,6-trisubstituted phenyl group. Suitable substituents for any substituted phenyl group within the 1,3-disubstituted imidazolinylidene group or 1,3-disubstituted imidazolidinylidene group can include any $C_1$ to $C_{10}$ hydrocarbyl group, or alternatively, any $C_1$ to $C_5$ hydrocarbyl group. In some aspects, each hydrocarbyl substituent independently can be a methyl group, ethyl group, n-propyl group, iso-propyl group, n-butyl group, sec-butyl group, or tert-butyl group; alternatively, a methyl group, ethyl group, n-butyl group, sec-butyl group, or tert-butyl group; alternatively, a methyl group; alternatively, an ethyl group, alternatively, an isopropyl group; or alternatively, a tert-butyl group. In some aspects, each substituted aromatic group of the 1,3-disubstituted imidazolinylidene group or 1,3-disubstituted imidazolidinylidene group independently can be a 2,6-diisopropylphenyl group or a 2,4,6-trimethyl-phenyl group; alternatively, a 2,6-diisopropylphenyl group; or alternatively, a 2,4,6-trimethylphenyl group.

In various aspects, each X of the compound having the structure $L^1L^2X_2Ru=CHR^1$ independently can be chloride, bromide, or iodide. In an aspect, X can be chloride. In another aspect, X can be bromide. In yet another aspect, X can be iodide. $R^1$ of the compound having the structure $L^1L^2X_2Ru=CHR^1$ can be hydrogen or a $C_1$ to $C_{20}$ hydrocarbyl group. In some aspects, $R^1$ can be a methyl group, an ethyl group, an isopropyl group, a tert-butyl group, a phenyl group, a 2-methyl-2-propene group, or a 2,2-diphenylethene group. In other aspects, $R^1$ can be a tert-butyl group, a phenyl group, a 2-methyl-2-propene group, or a 2,2-diphenylethene group; alternatively, hydrogen; alternatively, a tert-butyl group; alternatively, a phenyl group; alternatively, a tert-butyl group; alternatively, a phenyl group; alternatively, a 2-methyl-2-propene group; or alternatively, a 2,2-diphenylethene group.

In some non-limiting aspects, the ruthenium carbene based metathesis catalyst system can comprise dichloro (phenylmethylene) bis(tricyclohexyl phosphine) ruthenium, dichloro(3-methyl-2-butenylidene) bis(tricyclohexyl phosphine) ruthenium, dichloro(3-methyl-2-butenylidene) bis(tricyclopentyl phosphine) ruthenium, 1,3-bis-(2,4,6-trimethylphenyl)-2-(imidazolidinylidene)(phenyl-methylene) dichloro(tricyclohexyl phosphine) ruthenium, or 1,3-bis-(2,6-diisopropylphenyl)-2-(imidazolidinylidene)(phenylmethylene)dichloro(tricyclohexyl phosphine) ruthenium. In some aspects, the ruthenium carbene based metathesis catalyst system can comprise dichloro(phenylmethylene) bis(tricyclohexyl phosphine) ruthenium; alternatively, dichloro(3-methyl-2-butenylidene) bis(tricyclohexyl phosphine) ruthenium; alternatively, 1,3-bis-(2,4,6-trimethylphenyl)-2-(imidazolidinyl-idene)(phenylmethylene)dichloro(tricyclohexyl phosphine) ruthenium; or alternatively, 1,3-bis-(2,6-diisopropylphenyl)-2-(imidazolidinylidene) (phenylmethylene)dichloro(tricyclohexyl phosphine) ruthenium.

In an aspect, a molybdenum carbene based metathesis catalyst system can comprise a compound having the structure $Mo(=CHR^2)(NAr)(OR^3)_2$, wherein $R^2$ is a hydrogen or hydrocarbyl group, Ar is a substituted aromatic ring, and $R^3$ is a hydrocarbyl group or a halogenated hydrocarbyl group. Generally, the compound in the molybdenum carbene based metathesis catalyst system having the structure $Mo(=CHR^2)(NAr)(OR^3)_2$ can be described using any combination of $R^2$, Ar, and $R^3$ described herein.

In some aspects, $R^2$ of the compound having the structure $Mo(=CHR^2)(NAr)(OR^3)_2$ can be hydrogen or a $C_1$ to $C_{20}$ hydrocarbyl group, or alternatively, a $C_1$ to $C_{20}$ hydrocarbyl group. In some aspects, $R^2$ can be a methyl group, an ethyl group, an isopropyl group, a tert-butyl group, a phenyl group, a 2-methyl-2-propene group, or a 2,2-diphenylethene group. In other aspects, $R^2$ can be a tert-butyl group, a phenyl group, a 2-methyl-2-propene group, or a 2,2-diphenylethene group; alternatively, a tert-butyl group or a phenyl group; alternatively, hydrogen; alternatively, a tert-butyl group; alternatively, a phenyl group; alternatively, a 2-methyl-2-propene group; or alternatively, a 2,2-diphenylethene group.

In an aspect, the substituted aromatic ring, Ar, of the compound having the structure $Mo(=CHR^2)(NAr)(OR^3)_2$ can be a $C_6$ to $C_{30}$ aromatic group, or alternatively, a $C_6$ to $C_{20}$ aromatic group. In some aspects, each substituent of the substituted aromatic ring, Ar, independently can be a $C_6$ to $C_{20}$ hydrocarbyl group, a $C_1$ to $C_{10}$ hydrocarbyl group, or a $C_1$ to $C_5$ hydrocarbyl group. In some aspects, the substituted aromatic ring, Ar, can be a 2-substituted phenyl group, a 2,6-disubstituted phenyl group, or a 2,4,6-trisubstituted phenyl group. In an aspect, each substituent of the substituted aromatic ring independently can be a methyl group, an ethyl group, an isopropyl group, a tert-butyl group, or a neopentyl group; alternatively, a methyl group, an isopropyl group, or a tert-butyl group; alternatively, a methyl group or an isopropyl group. In some aspects, each substituent of the substituted aromatic ring independently can be a methyl group; alternatively, an isopropyl group; or alternatively, a tert-butyl group. In some non-limiting aspects, the substituted aromatic ring, Ar, can be a 2-tert-butylphenyl group, a 2,6-dimethylphenyl group, a 2,6-diisopropylphenyl group, or a 2,4,6-trimethyl phenyl group; alternatively, a 2-tert-butylphenyl group; alternatively, a 2,6-dimethylphenyl group; alternatively, a 2,6-diisopropylphenyl group; or alternatively, a 2,4,6-trimethyl phenyl group.

In an aspect, each $R^3$ of the compound having the structure $Mo(=CHR^2)(NAr)(OR^3)_2$ independently can be a $C_1$ to $C_{10}$ organic group, or alternatively, a $C_1$ to $C_5$ organic group. In some aspects, the $C_1$ to $C_{10}$ or $C_1$ to $C_5$ organic group can be a hydrocarbylhalyl group (a group consisting of hydrogen, carbon, and halogen atoms); alternatively, a hydrocarbylfluoryl group (a group consisting of hydrogen, carbon, and fluorine atoms); or alternatively, a hydrocarbyl group. In an aspect, the halogen atoms of the hydrocarbylhalyl group can be fluorine, chlorine, bromine, iodine, or any combination thereof; alternatively, fluorine; alternatively, chlorine; alternatively, bromine; or alternatively, iodine. In some aspects, each $R^3$ independently can be a tert-butyl group or a hexafluoro-tert-butyl group. In other aspects, $(OR^3)_2$ can represent a single organic group wherein the two $R^3$ groups attached to the oxygen atoms are connected via a bond between any divalent, trivalent, or tetravalent atom within the $R^3$ groups. In further aspects, $(OR^3)_2$ can represent a single organic group wherein the two $R^3$ groups attached to the oxygen atoms are connected via a carbon-carbon bond between any carbon atom of the two $R^3$ groups.

In an aspect, the molybdenum carbene based metathesis catalyst system can comprise $Mo(=CH-C(CH_3)_3)(N-2,6-diisopropylphenyl)(OC(CH_3)_3)$, $Mo(=CH-C(CH_3)_2(C_6H_5))(N-2,6-diiso-propylphenyl)(OC(CH_3)_3)$, $Mo(=CH-C(CH_3)_3)(N-2,6-diisopropylphenyl)(OC(CH_3)(CF_3)_2)$, or $Mo(=CH-C(CH_3)_2(C_6H_5))(N-2,6-diisopropylphenyl)(OC(CH_3)(CF_3)_2)$. In other aspects, the molybdenum carbene based metathesis catalyst system can comprise $Mo(=CH-C(CH_3)_3)(N-2,6-diiso-propylphenyl)(OC(CH_3)_3)$; alternatively, $Mo(=CH-C(CH_3)_2(C_6H_5))(N-2,6-diisopropylphenyl)-(OC(CH_3)_3)$; alternatively, $Mo(=CH-C(CH_3)_3)(N-2,6-diisopropylphenyl)(OC(CH_3)(CF_3)_2)$; or alternatively, $Mo(=CH-C(CH_3)_2(C_6H_5))(N-2,6-diisopropylphenyl)(OC(CH_3)(CF_3)_2)$.

Optionally, the metal carbene based metathesis catalyst system can further comprise a support. Illustrative supports can include alumina, silica, silica-alumina, and aluminum-phosphate, amongst other solid oxide materials. Additionally, the support can comprise a polymer, and the metal carbene metathesis catalyst compound can be tethered to the support via any of the ligands which do not contain the metal-carbon double bond.

Dehydroformylation Catalyst Systems

While not limited thereto, the dehydroformylation catalyst systems disclosed herein can be used in oxidative dehydroformylation processes to convert Cn aldehyde compounds to 1-decene. The catalyst system can utilize a pre-formed or pre-synthesized transition metal complex, or one in which the components are added together to generate the complex and catalyst in-situ. Thus, for example, the catalyst system can comprise any suitable transition metal compound, any suitable phosphine, and any suitable heteroatomic acid or heteroatomic acid derivative. Generally, the transition metal compound, the phosphine, and the heteroatomic acid or heteroatomic acid derivative are independent elements of the catalyst system and are independently described herein. Consequently, the catalyst system can be described utilizing any combination of the transition metal compound disclosed herein, the phosphine disclosed herein, and the heteroatomic acid or heteroatomic acid derivative disclosed herein. In another aspect, the catalyst system can comprise any suitable phosphine transition metal compound complex and any suitable heteroatomic acid or heteroatomic acid derivative. In this catalyst system aspect, the phosphine transition metal compound complex and the heteroatomic acid or heteroatomic acid derivative are independent elements of the catalyst system and are independently described herein. Consequently, the catalyst system can be described utilizing any combination of the phosphine transition metal compound complex disclosed herein and the heteroatomic acid or heteroatomic acid derivative disclosed herein.

The transition metal of the transition metal compound or the phosphine transition metal compound complex can be a Group 3 to Group 10 transition metal, a Group 4 to Group 11 transition metal, a Group 4 to Group 9 transition metal, a Group 8 to Group 10 transition metal, or a Group 9 transition metal. For instance, the transition metal of the transition metal compound or the phosphine transition metal compound complex can be cobalt, rhodium, or iridium; alternatively, cobalt; alternatively, rhodium; or alternatively, iridium. Accordingly, in an aspect of this invention, the transition metal compound or the transition metal compound of the phosphine transition metal compound complex can comprise a rhodium compound, non-limiting examples of which can include an olefin rhodium alkoxide complex, a cyclodiene rhodium alkoxide complex, or any combination thereof; alternatively, an olefin rhodium alkoxide complex; or alternatively, a cyclodiene rhodium alkoxide complex.

In one aspect, the phosphine or the phosphine of the phosphine transition metal compound complex can be a monophosphine. Illustrative and non-limiting examples of monophosphines include an alkyl phosphine (e.g., trimethylphosphine, triethylphosphine, triisopropylphosphine, triadamantylphosphine, and the like), an aryl phosphine (e.g., triphenylphosphine, tri-p-tolylphosphine, and the like), or any combination thereof.

In another aspect, the phosphine or the phosphine of the phosphine transition metal compound complex can be a diphosphine having the following structure:

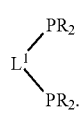

(I)

In structure (I), $L^1$ can be any suitable linking group or any linking group disclosed herein, and each R independently can be H or any $C_1$ to $C_{18}$ hydrocarbyl group, $C_1$ to $C_{18}$ hydrocarboxy group, or $C_1$ to $C_{13}$ hydrocarbylaminyl group disclosed herein. For instance, each R independently can be H or a $C_1$ to $C_{12}$ hydrocarbyl group; alternatively, H or a $C_1$ to $C_6$ hydrocarbyl group; alternatively, H or a $C_1$ to $C_{18}$ alkyl group, $C_2$ to $C_{18}$ alkenyl group, $C_6$ to $C_{18}$ aryl group, or $C_7$ to $C_{18}$ aralkyl group; or alternatively, H or a $C_1$ to $C_5$ alkyl group, $C_2$ to $C_5$ alkenyl group, $C_6$ to $C_8$ aryl group, or $C_7$ to $C_8$ aralkyl group. Each R independently in structure (I) can be, in certain aspects, H, a methyl group, an ethyl group, a propyl group, a butyl group, a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group, a benzyl group, or a naphthyl group. In other aspects, each R independently can be H, a methyl group, an ethyl group, a propyl group, a butyl group, a pentyl group, a hexyl group, a heptyl group, an octyl group, a nonyl group, or a decyl group; alternatively, H, an ethenyl group, a propenyl group, a butenyl group, a pentenyl group, a hexenyl group, a heptenyl group, an octenyl group, a nonenyl group, or a decenyl group; or alternatively, H, a phenyl group, a tolyl group, a benzyl group, or a naphthyl group.

A hydrocarboxy group is used generically herein to include, for instance, alkoxy, aryloxy, aralkoxy, -(alkylene, arylene, or aralkylene)-O-(alkyl, aryl, or aralkyl) groups, and —O(CO)-(hydrogen or hydrocarbyl) groups, and these groups can comprise up to about 18 carbon atoms (e.g., $C_1$ to $C_{18}$, $C_1$ to $C_{10}$, or $C_1$ to $C_8$ hydrocarboxy groups). Cyclic groups also are included. Illustrative and non-limiting examples of hydrocarboxy groups can include, but are not limited to, a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, a neo-pentoxy group, a phenoxy group, a toloxy group, a xyloxy group, a 2,4,6-trimethylphenoxy group, a benzoxy group, an acetylacetonate group (acac), a formate group, an acetate group, a stearate group, an oleate group, a benzoate group, a tetrahydrofuran group, a 1,4-dioxane group, and the like. In an aspect, the hydrocarboxy group which can be a R in formula (I) can be a methoxy group; alternatively, an ethoxy group; alternatively, an n-propoxy group; alternatively, an isopropoxy group; alternatively, an n-butoxy group; alternatively, a sec-butoxy group; alternatively, an isobutoxy group; alternatively, a tert-butoxy group; alternatively, an n-pentoxy group; alternatively, a 2-pentoxy group; alternatively, a 3-pentoxy group; alternatively, a 2-methyl-1-butoxy group; alternatively, a tert-pentoxy group; alternatively, a 3-methyl-1-butoxy group, alternatively, a 3-methyl-2-butoxy group; alternatively, a neo-pentoxy group; alternatively, a phenoxy group; alternatively, a toloxy group; alternatively, a xyloxy group; alternatively, a 2,4,6-trimethylphenoxy group; alternatively, a benzoxy group; alternatively, an acetylacetonate group; alternatively, a formate group; alternatively, an acetate group; alternatively, a stearate group; alternatively, an oleate group; alternatively, a benzoate group; alternatively, a tetrahydrofuran group; or alternatively, a 1,4-dioxane group.

The term hydrocarbylaminyl group is used generically herein to refer collectively to, for instance, alkylaminyl, arylaminyl, aralkylaminyl, dialkylaminyl, diarylaminyl, diaralkylaminyl, -(alkylene, arylene, or aralkylene)-N-(alkyl, aryl, or aralkyl) groups, and cyclic and aromatic amine groups (e.g., piperidine groups, pyrrole groups), and unless otherwise specified, the hydrocarbylaminyl groups can comprise up to about 18 carbon atoms (e.g., $C_1$ to $C_{18}$, $C_1$ to $C_{10}$, or $C_1$ to $C_8$ hydrocarbylaminyl groups). Accordingly, hydrocarbylaminyl is intended to cover both (mono)hydrocarbylaminyl and dihydrocarbylaminyl groups. In some aspects, the hydrocarbylaminyl group can be, for instance, a methylaminyl group (—NHCH$_3$), an ethylaminyl group (—NHCH$_2$CH$_3$), an n-propylaminyl group (—NHCH$_2$CH$_2$CH$_3$), an iso-propylaminyl group (—NHCH(CH$_3$)$_2$), an n-butylaminyl group (—NHCH$_2$CH$_2$CH$_2$CH$_3$), a t-butylaminyl group (—NHC(CH$_3$)$_3$), an n-pentylaminyl group (—NHCH$_2$CH$_2$CH$_2$CH$_2$CH$_3$), a neo-pentylaminyl group (—NHCH$_2$C(CH$_3$)$_3$), a phenylaminyl group (—NHC$_6$H$_5$), a tolylaminyl group (—NHC$_6$H$_4$CH$_3$), or a xylylaminyl group (—NHC$_6$H$_3$(CH$_3$)$_2$); alternatively, a methylaminyl group; alternatively, an ethylaminyl group; alternatively, a propylaminyl group; or alternatively, a phenylaminyl group. In other aspects, the hydrocarbylaminyl group which can be, for instance, a dimethylaminyl group (—N(CH₃)₂), a diethylaminyl group (—N(CH₂CH₃)₂), a di-n-propylaminyl group (—N(CH₂CH₂CH₃)₂), a di-isopropylaminyl group (—N(CH(CH₃)₂)₂), a di-n-butylaminyl group (—N(CH₂CH₂CH₂CH₃)₂), a di-t-butylaminyl group (—N(C(CH₃)₃)₂), a di-n-pentylaminyl group (—N(CH₂CH₂CH₂CH₂CH₃)₂), a di-neo-pentylaminyl group (—N(CH₂C(CH₃)₃)₂), a di-phenylaminyl group (—N(C₆H₅)₂), a di-tolylaminyl group (—N(C₆H₄CH₃)₂), or a di-xylylaminyl group (—N(C₆H₃(CH₃)₂)₂); alternatively, a dimethylaminyl group; alternatively, a di-ethylaminyl group; alternatively, a di-n-propylaminyl group; or alternatively, a di-phenylaminyl group.

In one aspect, the phosphine or the phosphine of the phosphine transition metal compound complex can comprise (or consist essentially of, or consist of) a 1,6-bis(dihydro-carbylphosphinyl)hexane, a substituted 1,6-bis(dihydrocarbylphosphinyl)hexane, a (1,3-phenylenedi-1,1-ethanediyl)bis(dihydrocarbylphosphine), a substituted (1,3-phenylenedi-1,1-ethanediyl)-bis(dihydrocarbylphosphine), a 1,8-anthracenediylbis(dihydrocarbylphosphine), a substituted 1,8-anthracenediylbis(dihydrocarbylphosphine), a 1,8-tetradecahydroanthracenediylbis(dihydrocarbyl-phosphine), a substituted 1,8-tetradecahydroanthracenediylbis(dihydrocarbylphosphine), a (methylenedi-2,1-phenylene)bis(dihydrocarbylphosphine), a substituted (methylenedi-2,1-phenylene)bis(dihydrocarbylphosphine), a 9H-xanthene-4,5-diylbis(dihydrocarbylphosphine), or a substituted 9H-xanthene-4,5-diylbis(dihydrocarbylphosphine). For example, the phosphine or the phosphine of the phosphine transition metal compound complex can comprise (or consist essentially of, or consist of) a 1,6-bis(dihydrocarbylphosphinyl)hexane; alternatively, a substituted 1,6-bis(dihydrocarbylphosphinyl)hexane; alternatively, a (1,3-phenylenedi-1,1-ethanediyl)-bis(dihydrocarbylphosphine); alternatively, a substituted (1,3-phenylenedi-1,1-ethanediyl)bis-(dihydrocarbylphosphine); alternatively, a 1,8-anthracenediylbis(dihydrocarbylphosphine); alternatively, a substituted 1,8-anthracenediylbis(dihydrocarbylphosphine); alternatively, a 1,8-tetradecahydroanthracenediylbis(dihydrocarbylphosphine); alternatively, a substituted 1,8-tetradecahydroanthracenediylbis(dihydrocarbylphosphine); alternatively, a (methylenedi-2,1-phenylene)bis(dihydrocarbylphosphine); alternatively, a substituted (methylenedi-2,1-phenylene)bis(dihydrocarbylphosphine); alternatively, a 9H-xanthene-4,5-diylbis(dihydrocarbyl-phosphine); or alternatively, a substituted 9H-xanthene-4,5-diylbis(dihydrocarbylphosphine). Each hydrocarbyl independently can be any suitable hydrocarbyl group or any $C_1$ to $C_{18}$ hydrocarbyl group, $C_1$ to $C_{12}$ hydrocarbyl group, or $C_1$ to $C_6$ hydrocarbyl group disclosed herein.

In another aspect, the phosphine or the phosphine of the phosphine transition metal compound complex can comprise (or consist essentially of, or consist of) a 1,6-bisphosphinylhexane, a substituted 1,6-bisphosphinylhexane, a (1,3-phenylenedi-1,1-ethanediyl)bis(phosphine), a substituted (1,3-phenylenedi-1,1-ethanediyl)bis(phosphine), a 1,8-anthracenediylbis(phosphine), a substituted 1,8-anthracenediylbis(phosphine), a 1,8-tetradecahydroanthracenediylbis(phosphine), a substituted 1,8-tetradecahydroanthracenediylbis(phosphine), a (methylenedi-2,1-phenylene)bis(phosphine), a substituted (methylenedi-2,1-phenylene)bis(phosphine), a 9H-xanthene-4,5-diylbis(phosphine), or a substituted 9H-xanthene-4,5-diylbis(phosphine). For example, the phosphine or the phosphine of the phosphine transition metal compound complex can comprise (or consist essentially of, or consist of) a 1,6-bisphosphinylhexane; alternatively, a substituted 1,6-bisphosphinylhexane; alternatively, a (1,3-phenylenedi-1,1-ethanediyl)bis(phosphine); alternatively, a substituted (1,3-phenylenedi-1,1-ethanediyl)bis(phosphine); alternatively, a 1,8-anthracenediylbis(phosphine); alternatively, a substituted 1,8-anthracenediylbis(phosphine); alternatively, a 1,8-tetradecahydroanthracenediylbis(phosphine); alternatively, a substituted 1,8-tetradecahydroanthracenediylbis(phosphine); alternatively, a (methylenedi-2,1-phenylene)bis(phosphine); alternatively, a substituted (methylenedi-2,1-phenylene)bis(phosphine); alternatively, a 9H-xanthene-4,5-diylbis(phosphine); or alternatively, a substituted 9H-xanthene-4,5-diylbis(phosphine).

In yet another aspect, the phosphine or the phosphine of the phosphine transition metal compound complex can comprise (or consist essentially of, or consist of) a (9,9-dimethyl-9H-xanthen-4,5-diyl)bis(phosphine) or a substituted (9,9-dimethyl-9H-xanthen-4,5-diyl)bis(phosphine); alternatively, a (9,9-dimethyl-9H-xanthen-4,5-diyl)bis(phosphine); or alternatively, a substituted (9,9-dimethyl-9H-xanthen-4,5-diyl)bis(phosphine).

In still another aspect, the phosphine or the phosphine of the transition metal compound complex can have any one of the following structures, wherein Ph is a phenyl group, and each R independently can be H or any $C_1$ to $C_{18}$ hydrocarbyl group, $C_1$ to $C_{18}$ hydrocarboxy group, or $C_1$ to $C_{18}$ hydrocarbylaminyl group disclosed herein (e.g., H, a $C_1$ to $C_{12}$ hydrocarbyl group, a $C_1$ to $C_{12}$ hydrocarboxy group, or $C_1$ to $C_{12}$ hydrocarbylaminyl group; alternatively, H or a $C_1$ to $C_6$ hydrocarbyl group; alternatively, H or a $C_1$ to $C_{18}$ alkyl group, $C_2$ to $C_{18}$ alkenyl group, $C_6$ to $C_{18}$ aryl group, or $C_7$ to $C_{18}$ aralkyl group; or alternatively, H or a $C_1$ to $C_5$ alkyl group, $C_2$ to $C_8$ alkenyl group, $C_6$ to $C_8$ aryl group, or $C_7$ to $C_8$ aralkyl group):

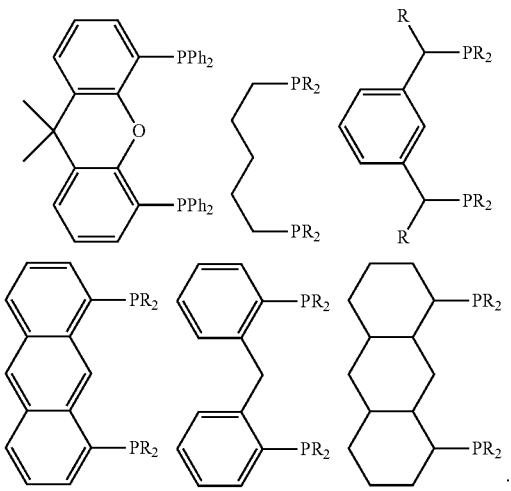

In another aspect, the phosphine or the phosphine of the transition metal compound complex can have any one of the following structures, wherein Ph is a phenyl group, Me is a methyl group, Ar is a $C_6$ to $C_{18}$ aromatic group (e.g., a $C_6$ to $C_{12}$ aromatic group), each R independently can be H or any $C_1$ to $C_{18}$ hydrocarbyl group, $C_1$ to $C_{18}$ hydrocarboxy group, or $C_1$ to $C_{18}$ hydrocarbylaminyl group disclosed herein, and L can be any $C_1$ to $C_{10}$ (e.g., any $C_1$ to $C_5$) linking group disclosed herein.

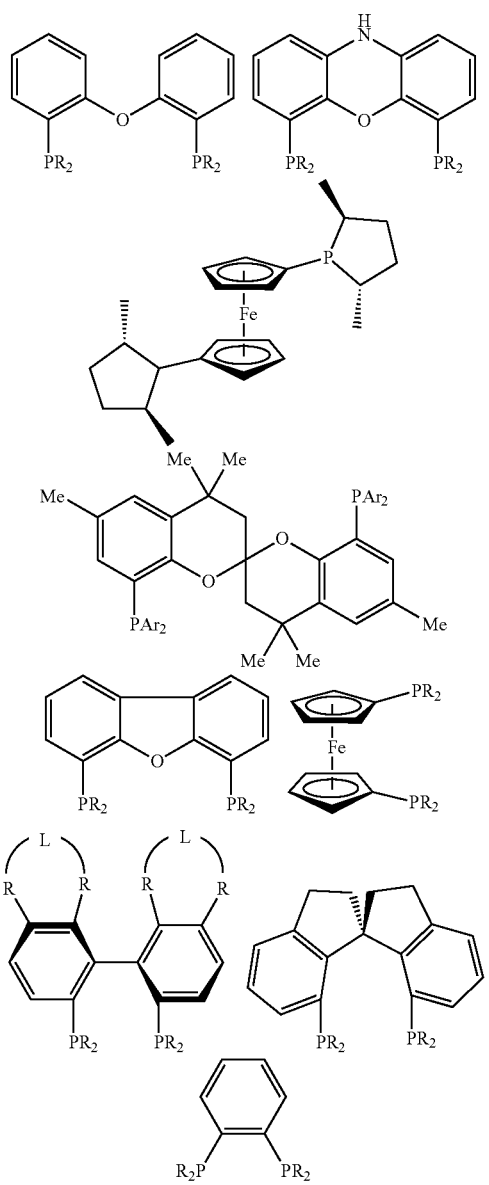

Any suitable linking group (L or $L^1$ in the above structures/formulas) can be used. For instance, the linking group can be any hydrocarbylene group (e.g., alkylene, cycloalkylene, or arylene), hydrocarboxy group (e.g., ether or cyclic ether), or hydrocarbylaminyl group disclosed herein.

The specific heteroatomic acid or heteroatomic acid derivative used in the catalyst system is not particularly limited. In some aspects, the heteroatomic acid or heteroatomic acid derivative can comprise a carboxylic acid, an alcohol, a mineral acid, an ammonium salt, an amine, a thiol, and the like, as well as combinations thereof. For instance, the heteroatomic acid or heteroatomic acid derivative can comprise a carboxylic acid or carboxylic acid derivative. In one aspect, the carboxylic acid or carboxylic acid derivative can be an aliphatic carboxylic acid or carboxylic acid derivative, while in another aspect, the carboxylic acid or carboxylic acid derivative can be an aromatic carboxylic acid or carboxylic acid derivative. The carboxylic acid can be any suitable $C_1$ to $C_{24}$ carboxylic acid or any $C_1$ to $C_{24}$ carboxylic acid disclosed herein, either substituted or unsubstituted. Non-limiting examples of carboxylic acids can include formic acid, acetic acid, propionic acid, butanoic acid, pentanoic acid, hexanoic acid, stearic acid, acrylic acid, methacrylic acid, cinnamic acid, benzoic acid, salicylic acid, adipic acid, citric acid, or any combination thereof.

As used herein, "heteroatomic acid derivative" and "carboxylic acid derivative" are meant to encompass salts and esters of heteroatomic acids and carboxylic acids, respectively. For instance, the carboxylic acid derivative can be a carboxylic acid salt, a carboxylic acid ester, or any combination thereof; alternatively, a carboxylic acid salt; or alternatively, a carboxylic acid ester. Typical carboxylic acid salts can include alkali metal or alkaline earth metal salts (e.g., sodium, calcium, magnesium) of the carboxylic acid, while esters refers to compounds where at least one —OH group of the carboxylic acid is replaced by an alkoxy group (e.g., formates, acetates, hexanoates, stearates, acrylates, cinnamates, benzoates, and the like). Similar to the carboxylic acid, the carboxylic acid derivative can be any suitable $C_1$ to $C_{24}$ carboxylic acid derivative or any $C_1$ to $C_{24}$ carboxylic acid derivative disclosed herein, either substituted or unsubstituted. In an aspect, each substituent can be a $C_1$ to $C_8$ hydrocarbyl group, a $C_1$ to $C_5$ hydrocarbyl group, a $C_1$ to $C_8$ alkyl group, or a $C_1$ to $C_5$ alkyl group. In an aspect, the carboxylic acid ester can be a methyl ester, an ethyl ester, a propyl ester, or a butyl ester of any carboxylic acid described herein. As a representative example, the carboxylic acid or carboxylic acid derivative can comprise benzoic acid (or a substituted benzoic acid) or a salt or ester of benzoic acid (or a salt or ester of a substituted benzoic acid).

In circumstances where the catalyst system comprises a transition metal compound, a phosphine, and a heteroatomic acid or heteroatomic acid derivative, the minimum molar ratio of the transition metal (of the transition metal compound) to the phosphine can be 0.2:1, 0.5:1, 0.8:1, or 0.95:1; additionally or alternatively, the maximum molar ratio of the transition metal to the phosphine can be 5:1, 4:1, 3:1, or 2.5:1. In an aspect, the transition metal (of the transition metal compound) to phosphine (or diphosphine) molar ratio can be in a range from any minimum transition metal to phosphine molar ratio disclosed herein to any maximum transition metal to phosphine molar ratio disclosed herein. In some non-limiting aspects, the molar ratio can be in a range from about 0.2:1 to about 5:1, from about 0.2:1 to about 3:1, from about 0.5:1 to about 4:1, or from about 0.95:1 to about 2.5:1. Other molar ratios of the transition metal to the phosphine (or diphosphine) are readily apparent from this disclosure.

The amount of the heteroatomic acid or heteroatomic acid derivative used in the catalyst system is not particularly limited, but generally, the minimum molar ratio of the transition metal (of the transition metal compound or the phosphine transition metal compound complex) to the heteroatomic acid or heteroatomic acid derivative can be 0.8:1, 0.85:1, 0.9:1, or 0.95:1; additionally or alternatively, the maximum molar ratio of the transition metal to the heteroatomic acid or heteroatomic acid derivative can be 5:1, 3:1, 2:1, or 1.5:1. In an aspect, the transition metal (of the transition metal compound or the phosphine transition metal compound complex) to heteroatomic acid or heteroatomic acid derivative molar ratio can be in a range from any minimum transition metal to heteroatomic acid or heteroatomic acid derivative molar ratio disclosed herein to any maximum transition metal to heteroatomic acid or heteroatomic acid derivative molar ratio disclosed herein. In some non-limiting aspects, the molar ratio can be in a range from about 0.8:1 to about 5:1, from about 0.85:1 to about 3:1, from about 0.9:1 to about 2:1, or from about 0.95:1 to about 1.5:1. Other molar ratios of the transition metal (of the transition metal compound or the phosphine transition metal compound complex) to the heteroatomic acid or heteroatomic acid derivative are readily apparent from this disclosure.

Beneficially, the dehydroformylation catalyst system can further comprise an acceptor, also referred to as an acceptor olefin, which can increase the yield of the normal alpha olefin in the processes described in greater detail hereinbelow. In general, the acceptor can be any suitable compound having at least one carbon-carbon double bond. In an aspect, the acceptor can have at least 2 carbon atoms, at least 3 carbon atoms, at least 4 carbon atoms, or at least 5 carbon atoms. In some aspects, the acceptor can have a maximum of 100 carbon atoms, 80 carbon atoms, 60 carbon atoms, 50 carbon atoms, 40 carbon atoms, 30 carbon atoms, 25 carbon atoms, 20 carbon atoms, 15 carbon atoms, or 10 carbon atoms. Generally, the acceptor can have from any minimum number of carbon atoms described herein to any maximum number of carbon atoms described herein. For example, in some non-limiting aspects, the acceptor (or acceptor olefin) can have from 2 to 100 carbon atoms, from 3 to 80 carbon atoms, from 4 to 60 carbon atoms, or from 5 to 60 carbon atoms. Other carbon atom number ranges can be readily envisioned from the present disclosure and are encompassed herein. Mixtures or combinations of more than one acceptor (or acceptor olefin) can be employed in the present invention.

In an aspect, the acceptor (or acceptor olefin) can be a hydrocarbon compound or, alternatively, a heteroatomic compound. In some aspects, the acceptor can be aliphatic or, alternatively, aromatic. In other aspects, the acceptor can be acyclic or, alternatively, cyclic.

The acceptor can have at least one carbon-carbon double bond. In one aspect, the acceptor has from 1 to 10 double bonds; alternatively, from 1 to 8 double bonds; alternatively, from 3 to 5 double bonds; or alternatively, from 2 to 4 double bonds. In another aspect, the acceptor can have only one carbon-carbon double bond; alternatively, only two double bonds; alternatively, only three double bonds; alternatively, only four double bonds; alternatively, only five double bonds; or alternatively, only six double bonds.

Representative and non-limiting examples of acceptors (or acceptor olefins) having only one carbon-carbon double bond can comprise, consist essentially of, or consist of, either singly or in any combination, ethylene, t-butyl ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, 1-undecene, 1-dodecene, 1-tridecene, 1-tetradecene, 1-pentadecene, a vinylidene, or styrene.

Representative and non-limiting examples of cyclic acceptor olefins acceptor having only one carbon-carbon double bond can comprise, consist essentially of, or consist of, either singly or in any combination, norbornene, cyclopentene, cyclohexene, cycloheptene, or cyclooctene. In some aspects, cyclic acceptor olefins having only one carbon-carbon double bond can comprise, consist essentially of, or consist of, norbornene; alternatively, cyclopentene; alternatively, cyclohexene; alternatively, cycloheptene; or alternatively, cyclooctene.

Illustrative examples of acceptor olefins having at least two carbon-carbon double bonds that can be employed in the catalyst systems and processes disclosed herein can comprise, consist essentially of, or consist of, either singly or in any combination, butadiene (1,3-butadiene), isoprene, 1,5-hexadiene, 1,7-octadiene, cyclobutadiene, cyclopentadiene, cyclohexadiene, cyclooctadiene, norbornadiene, vinylcyclohexene, vinylnorbornene, divinylbenzene, or cyclopentadiene dimer.

Hence, mixtures or combinations of more than one acceptor olefin can be employed. Accordingly, the acceptor olefin having at least two double bonds can comprise, consist essentially of, or consist of, either singly or in any combination, butadiene, isoprene, 1,5-hexadiene, 1,7-octadiene, cyclobutadiene, cyclopentadiene, cyclohexadiene, or cyclooctadiene; alternatively, norbornadiene, vinylcyclohexene, vinylnorbornene, or divinylbenzene; alternatively, butadiene; alternatively, isoprene; alternatively, 1,5-hexadiene; alternatively, 1,7-octadiene; alternatively, cyclobutadiene; alternatively, cyclopentadiene; alternatively, cyclohexadiene; alternatively, cyclooctadiene; alternatively, norbornadiene; alternatively, vinylcyclohexene; alternatively, vinylnorbornene; alternatively, divinylbenzene; or alternatively, cyclopentadiene dimer.

In an aspect, the acceptor olefin can comprise, consist essentially of, or consist of, one or more compounds having only three carbon-carbon double bonds. Illustrative non-limiting examples of such compounds can comprise, consist essentially of, or consist of, singly or in any combination, trivinylcyclohexane, trivinylbenzene, cycloheptatriene, dimethyl heptatriene, octatriene, cyclooctatriene, or cyclododecatriene. In one aspect, the acceptor olefin can comprise, consist essentially of, or consist of, trivinylcyclohexane. In another aspect, the acceptor olefin can comprise, consist essentially of, or consist of, trivinylbenzene. In another aspect, the acceptor olefin can comprise, consist essentially of, or consist of, cycloheptatriene. In another aspect, the acceptor olefin can comprise, consist essentially of, or consist of, dimethyl heptatriene. In another aspect, the acceptor olefin can comprise, consist essentially of, or consist of, octatriene. Yet, in another aspect, the acceptor olefin can comprise, consist essentially of, or consist of, cyclooctatriene. In still another aspect, the acceptor olefin can comprise, consist essentially of, or consist of, cyclododecatriene. Additionally, the acceptor can comprise benzene and other aromatic compounds, as well as suitable 1,n-1,x-alkyltrienes (linear alkyltrienes).

Acceptor olefins having four or more carbon-carbon bonds also are contemplated. For instance, the acceptor olefin can comprise, consist essentially of, or consist of, cyclooctatetraene; alternatively, cyclododecatetraene; alternatively, a polybutadiene; or alternatively, a combination of two or more of these compounds.

In some aspects, the acceptor can comprise, consist essentially of, or consist of, an unsaturated triglyceride, while in other aspects, the acceptor can comprise, consist essentially of, or consist of, an unsaturated natural source oil. In an aspect, the acceptor can comprise, consist essentially of, or consist of, either singly or in any combination, soybean oil, corn oil, castor bean oil, or canola oil. In other aspects, the acceptor can comprise an unsaturated carboxylic acid, an ester of an unsaturated carboxylic acid (e.g., methyl, ethyl ester, propyl, or butyl ester), or any combination thereof; alternatively, an unsaturated carboxylic acid; or alternatively, an ester of an unsaturated carboxylic acid. In some aspects, the unsaturated carboxylic acid, or the unsaturated carboxylic acid portion of the unsaturated carboxylic acid ester, which can be utilized as the aldehyde group acceptor can comprise, consist essentially of, or consist of, vinyl acetic acid, 3-pentenoic acid, maleic acid, fumaric acid, sorbic acid, caproleic acid, lauroleic acid, myristoleic acid, palmitoleic acid, oleic acid, ricinoleic acid, linoleic acid, linolenic acid, or any combination thereof. In yet another aspect, the acceptor can comprise an unsaturated carboxylic acid anhydride (e.g., maleic anhydride).

The acceptor also can comprise any suitable heteroatomic olefin compound, either singly or in combination. Representative and non-limiting examples of such heteroatomic olefin compounds include an enone, an enamine, an enol, an enamide (e.g., acrylamide), and the like, as well as combinations thereof.

Manufacturing Systems

A first (1-octene and 1-decene) manufacturing system provided herein can comprise 1) an ethylene oligomerization system configured to oligomerize ethylene in the presence of a catalyst system or catalyst system components to form a composition comprising an oligomer product, the oligomer product comprising from 20 to 80 mol % $C_6$ olefins, from 15 to 80 mol % $C_8$ olefins, and from 5 to 20 mol % $C_{10}$+ olefins, 2) a fractionation system configured to separate the composition comprising the oligomer product into i) a first oligomer composition comprising 1-hexene, ii) a second oligomer composition comprising 1-octene, and iii) a heavies stream comprising $C_{10}$+ olefins, 3) a metathesis system configured to contact a metathesis catalyst system with all or a portion of the first oligomer composition to form a first composition comprising $C_{10}$ linear internal olefins, 4) an isomerization hydrofunctionalization system configured to contact the $C_{10}$ linear internal olefins with an isomerization hydrofunctionalization catalyst system to form a second composition comprising a functionalized alkane, 5) a retro-hydrofunctionalization system configured to treat the functionalized alkane to form a third composition comprising 1-decene, and 6) a purification system configured to isolate a fourth composition comprising at least 90 mol % 1-decene from the third composition.

A second (1-hexene and 1-decene) manufacturing system provided herein can comprise 1) an ethylene oligomerization system configured to oligomerize ethylene in the presence of a catalyst system or catalyst system components to form a composition comprising an oligomer product, the oligomer product comprising at least 85 mol % $C_6$ olefins and at least 5 mol % $C_8$+ olefins, 2) a fractionation system configured to separate the composition comprising the oligomer product into a first oligomer composition comprising 1-hexene and a heavies stream comprising $C_8$+ olefins, 3) a metathesis system configured to contact a metathesis catalyst system with all or a portion of the first oligomer composition to form a first composition comprising $C_{10}$ linear internal olefins, 4) an isomerization hydrofunctionalization system configured to contact the $C_{10}$ linear internal olefins with an isomerization hydrofunctionalization catalyst system to form a second composition comprising a functionalized alkane, 5) a retro-hydrofunctionalization system configured to treat the functionalized alkane to form a third composition comprising 1-decene, and 6) a purification system configured to isolate a fourth composition comprising at least 90 mol % 1-decene from the third composition.

Generally, the features of the first manufacturing system and the second manufacturing system are the same as those described generally herein for the respective first process and second process. Thus, any features of the first process and the second process can be applied to the respective first manufacturing system and the second manufacturing system.

Optionally, the first manufacturing system (or the second manufacturing system) can further comprise a metathesis purification system configured to isolate a composition comprising $C_{10}$ linear internal olefins from the first composition prior to the isomerization hydrofunctionalization system. Also optionally, the first manufacturing system (or the second manufacturing system) can further comprise a isomerization hydrofunctionalization purification system configured to isolate a composition comprising functionalized alkane from the second composition prior to the retro-hydrofunctionalization system. Independently, these purification systems can comprise, for instance, extraction, filtration, evaporation, distillation, and the like, as well as any combination thereof.

Referring now to FIG. 1, which illustrates a 1-octene/1-decene manufacturing system 100 consistent with an aspect of the present disclosure. The system 100 can include an ethylene oligomerization system 110, a fractionation system 120, a metathesis system 130, an isomerization hydrofunctionalization system 150, a retro-hydrofunctionalization system 160, and a purification system 170. In FIG. 1, an ethylene feed stream 105 enters the ethylene oligomerization system 110. Other feed streams to the ethylene oligomerization system 110, such as for catalyst system or catalyst system components, reaction medium (if used), and hydrogen (if used) are not specifically shown in FIG. 1. It is understood by a skilled artisan that there may be many different inputs to the ethylene oligomerization system, and this disclosure is not limited only to those options described in reference to FIG. 1 or otherwise disclosed herein. In the ethylene oligomerization system 110, the ethylene introduced via ethylene feed stream 105 is oligomerized in the presence of a catalyst system (or catalyst system components) to form a composition 115 comprising an oligomer product, which is discharged from the ethylene oligomerization system 110. Generally, the oligomer product contains from 20 to 80 mol % $C_6$ olefins, from 15 to 80 mol % $C_8$ olefins, and from 5 to 20 mol % $C_{10}$+ olefins.

This composition 115 comprising the oligomer product enters a fractionation system 120, which separates the composition 115 into a heavies stream 122 comprising $C_{10}$+ olefins (and optionally, spent catalyst), a second oligomer composition 124 comprising 1-octene, and a first oligomer composition 125 comprising 1-hexene. The first oligomer composition 125 comprising 1-hexene can be split into a 1-hexene product stream 126 and a 1-hexene feed stream 128. Thus, all or a portion of the first oligomer composition 125 can be fed to the metathesis system 130 and contacted with a suitable metathesis catalyst system to form a first composition 135 comprising $C_{10}$ linear internal olefins, which exits the metathesis system 130.

In FIG. 1, the composition 135 comprising $C_{10}$ linear internal olefins enters the isomerization hydrofunctionalization system 150 and is contacted with an isomerization hydrofunctionalization catalyst system in the isomerization hydrofunctionalization system 150 to form a second composition 155 comprising functionalized alkanes. The resulting second composition 155 comprising functionalized alkanes is discharged from the isomerization hydrofunctionalization system 150 and is introduced into the retro-hydrofunctionalization system 160, in which the functionalized alkanes are treated to form a third composition 165 comprising 1-decene, which exits the retro-hydrofunctionalization system 160. If desired, recycle stream 162 from the retro-hydrofunctionalization system 160 can recycle carbon monoxide and/or hydrogen for use in the isomerization hydrofunctionalization system 150.

If desired, the system 100 of FIG. 1 can include the purification system 170. The third composition 165 comprising 1-decene exits the retro-hydrofunctionalization system 160 and enters the purification system 170, where a fourth composition 175 comprising at least 90 mol % 1-decene is produced and is discharged from the purification system 170.

Figure 2:
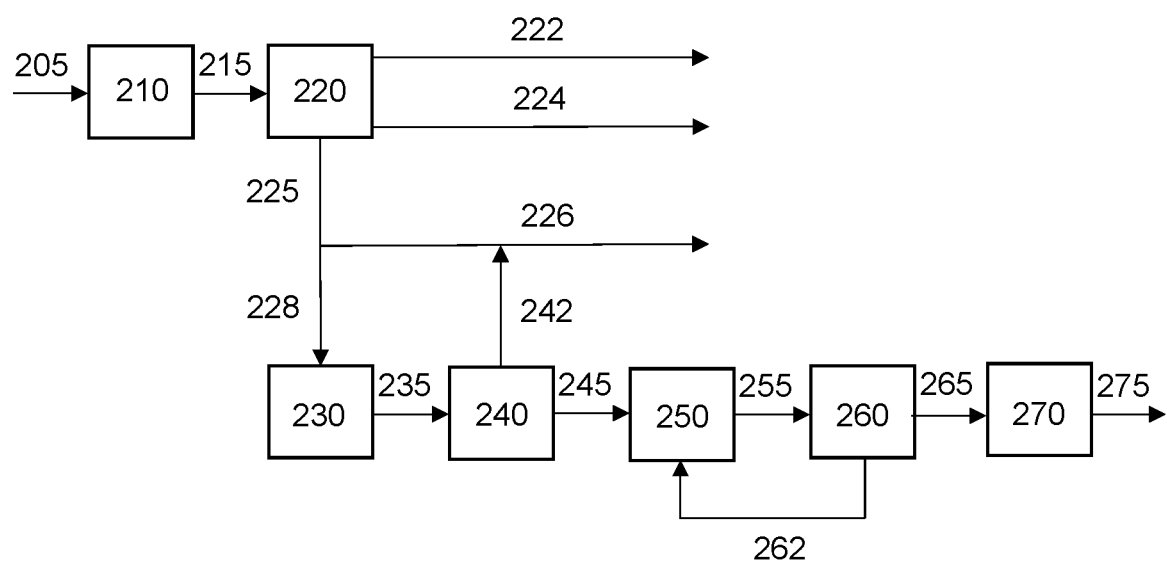
FIG. 2 illustrates a 1-octene/1-decene manufacturing system consistent with another aspect of the present disclosure.

Referring now to FIG. 2, which illustrates another 1-octene/1-decene manufacturing system 200 consistent with an aspect of the present disclosure. The system 200 can include an ethylene oligomerization system 210, a fractionation system 220, a metathesis system 230, an isomerization hydrofunctionalization system 250, a retro-hydrofunctionalization system 260, a purification system 270, an ethylene feed stream 205, a composition 215 comprising an oligomer product, a heavies stream 222 comprising $C_{10}+$ olefins (and optionally, spent catalyst), a second oligomer composition 224 comprising 1-octene, a first oligomer composition 225 comprising 1-hexene (which can be split into a 1-hexene product stream 226 and a 1-hexene feed stream 228), a second composition 255 comprising $C_{11}$ aldehydes, a third composition 265 comprising 1-decene, a recycle stream 262, and a fourth composition 275 comprising at least 90 mol % 1-decene, which are generally the same as described for the similarly numbered components in FIG. 1.

In FIG. 2, the composition 235 comprising $C_{10}$ linear internal olefins exits the metathesis system 230 and enters a metathesis purification system 240 configured to isolate a composition 245 comprising $C_{10}$ linear internal olefins, which exits the metathesis purification system 240 and enters the isomerization hydrofunctionalization system 250. A by-product stream 242 containing $C_6$ olefins is discharged from the metathesis purification system 240 and is combined with the 1-hexene product stream 226.

Figure 3:
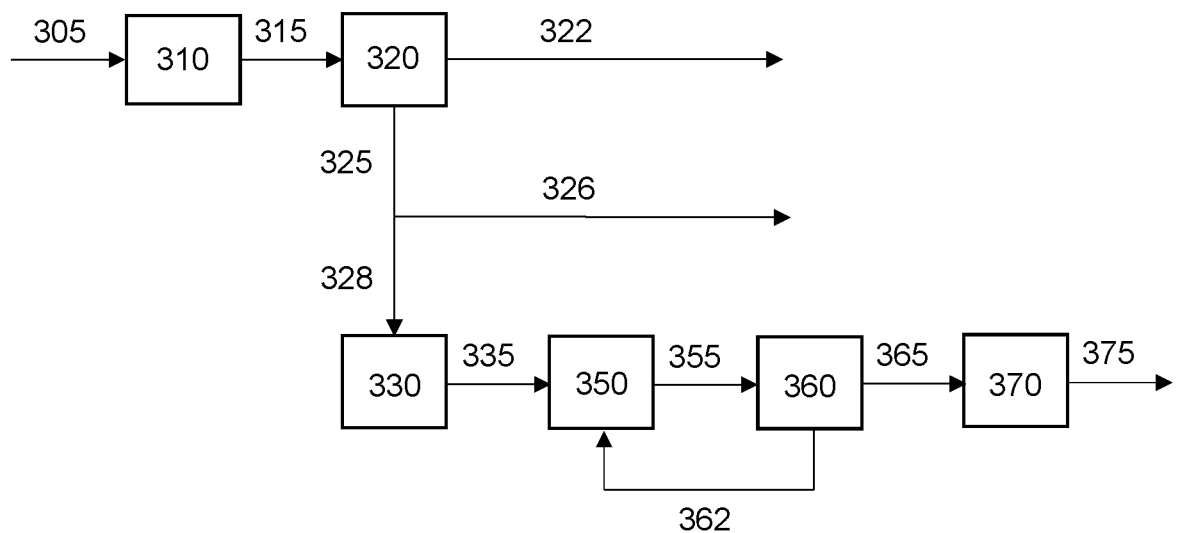
FIG. 3 illustrates a 1-hexene/1-decene manufacturing system consistent with yet another aspect of the present disclosure.

Referring now to FIG. 3, which illustrates a 1-hexene/1-decene manufacturing system 300 consistent with an aspect of the present disclosure. The system 300 can include a metathesis system 330, an isomerization hydrofunctionalization system 350, a retro-hydrofunctionalization system 360, a purification system 370, an ethylene feed stream 305, a first composition 335 comprising $C_{10}$ linear internal olefins, a second composition 355 comprising $C_{11}$ aldehydes, a third composition 365 comprising 1-decene, a recycle stream 362, and a fourth composition 375 comprising at least 90 mol % 1-decene, which are generally the same as described for the similarly numbered components in FIG. 1.

In FIG. 3, the ethylene feed stream 305 enters an ethylene oligomerization system 310. Other feed streams to the ethylene oligomerization system 310, such as for catalyst system or catalyst system components, reaction medium (if used), and hydrogen (if used) are not specifically shown in FIG. 3. It is understood by a skilled artisan that there may be many different inputs to the ethylene oligomerization system, and this disclosure is not limited only to those options described in reference to FIG. 3 or otherwise disclosed herein. In the ethylene oligomerization system 310, the ethylene introduced via ethylene feed stream 305 is oligomerized in the presence of a catalyst system (or catalyst system components) to form a composition 315 comprising an oligomer product, which is discharged from the ethylene oligomerization system 310. Generally, and unlike FIGS. 1-2, the oligomer product in FIG. 3 contains at least 85 mol % $C_6$ olefins and at least 5 mol % $C_8+$ olefins (selective 1-hexene production).

This composition 315 comprising the oligomer product enters a fractionation system 320, which separates the composition 315 into a heavies stream 322 comprising $C_8+$ olefins (and optionally, spent catalyst) and a first oligomer composition 325 comprising 1-hexene. The first oligomer composition 325 comprising 1-hexene can be split into a 1-hexene product stream 326 and a 1-hexene feed stream 328. Thus, all or a portion of the first oligomer composition 325 can be fed to the metathesis system 330 and contacted with a suitable metathesis catalyst system to form a first composition 335 comprising $C_{10}$ linear internal olefins, which exits the metathesis system 330.

EXAMPLES

The invention is further illustrated by the following examples, which are not to be construed in any way as imposing limitations to the scope of this invention. Various other aspects, modifications, and equivalents thereof which, after reading the description herein, can suggest themselves to one of ordinary skill in the art without departing from the spirit of the present invention or the scope of the appended claims.

Example 1

Reaction of 1-Dodecanol without an Acceptor

Example 1 was conducted by combining 1-dodecanol (0.2 mmol), [Rh(cod)OMe]$_2$ (2 mol %), 3-OMeBzOH (4 mol %), and Xantphos (4 mol %) in 0.4 mL toluene and heating the solution to 90° C. (see reaction scheme below). The reaction continued for 24 h before analyzing the crude reaction mixture by gas chromatography using durene as an internal standard to determine the amount of 1-undecene, 1-undecane, and undecene isomers present in the reaction mixture. Gas chromatography analysis determined that only 1-undecane was present in the reaction mixture (10 mol % yield).

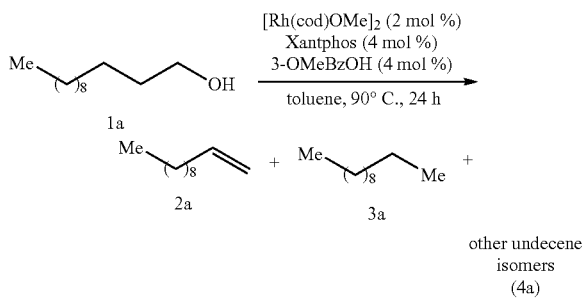

EXAMPLES 1A-1K

Reaction of 1-Dodecanol in the Presence of Various Acceptors

Examples 1A-1K utilized the general experimental procedure described above for Example 1, except that an acceptor (3 molar equivalents based on the primary alcohol) was used. Examples 1A-1K were conducted as single, individual experiments; results from each reaction are shown in Table II below. Surprisingly, Example 1K, which employed dimethylacrylamide as the acceptor, exhibited a dramatic and unexpected improvement to the selectivity of the reaction with respect to the $C_{(n-1)}$ olefin product, producing a 95% molar yield of the desired 1-undecene product, and only about 3 mol % of alkane and internal olefin byproducts. Moreover, Examples 1H-1J also demonstrated excellent selectivity, each having a yield of 1-undecene above 30%, using ethyl acrylate, t-butyl acrylate, and acrylamide, respectively.

TABLE II

| Example | Acceptor | 1-undecene | 1-undecane | Isomers |
|---|---|---|---|---|
| 1A | norbornadiene | 32 | — | 2 |
| 1B | norbornene | 18 | — | 8 |
| 1C | acetone | — | 15 | — |
| 1D | cyclopentanone | — | 30 | — |
| 1E | PhC(O)CF₃ | — | 12 | — |
| 1F | methyl vinyl ketone | 10 | 7 | 2 |
| 1G | acrylonitrile | 3 | 9 | — |
| 1H | ethyl acrylate | 33 | 1 | 1 |
| 1I | t-butyl acrylate | 41 | 2 | 1 |
| 1J | acrylamide | 35 | 2 | 1 |
| 1K | dimethylacrylamide | 95 | 1 | 2 |

Example 2

Oxidative Dehydroformylation of an Aldehyde Compound to Form an α-Olefin

Example 2 utilized the general experimental procedure described above for Inventive Example 1K (dimethylacrylamide), except that the primary alcohol compound reactant was substituted for aldehyde compound 4, only 1.5 equivalents of dimethylacrylamide were used, the amounts of [Rh(cod)OMe]₂ (0.5 mol %), 3-OMeBzOH (1 mol %), and Xantphos (1 mol %) were reduced, and the reaction time was only 3 h. Surprisingly, the α-olefin product was formed at a 94% yield in only 3 h, even though a comparatively small amount of the catalyst composition was used in the reaction.

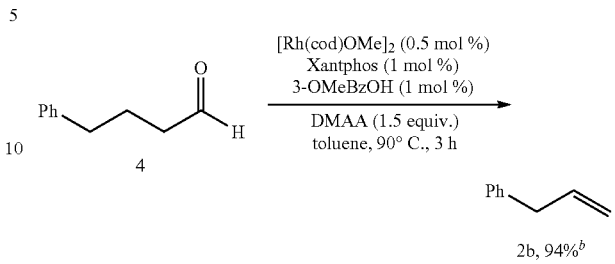

Constructive Example 3

In accordance with the first process and the second process disclosed herein, Constructive Example 3 demonstrates the conversion of 1-hexene to 1-decene via a metathesis (homogeneous), isomerization-hydroformylation (unligated), and dehydroformylation pathway as shown in the synthesis scheme below (where n=3).

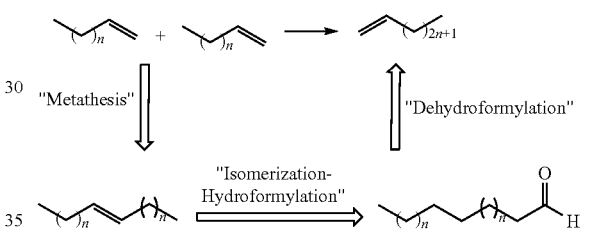

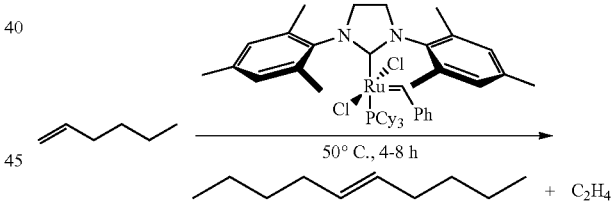

The reaction scheme for the homogeneous metathesis step is shown below.

The metathesis step can be performed as follows. In a drybox under an N₂ atmosphere, a 500 mL round bottom flask with a magnetic stir bar is charged with 1-hexene (250 mL, 168 g, ~2 mol). The flask is placed in an aluminum block on a temperature controlled heating plate at ~50° C. and allowed to equilibrate temperature. To this stirring solution, a Grubbs 2$^{nd}$ Generation Catalyst (dichloro [1,3-bis(2,4,6-trimethylphenyl)-2-imidazolidinylidene] (benzylidene) (tricyclohexyl-phosphine) ruthenium(II), 4.2 mg, 4.9 µmol) is added to initiate the reaction. Reaction progress can be monitored by taking aliquot samples and analyzing them by GC-FID for reaction equilibrium, which typically takes 4-8 hr. Any produced ethylene is allowed to bubble and leave the flask as it is not capped in the glovebox. Upon completion of the reaction, the solution is cooled, filtered, and the reaction contents distilled to isolate 5-decene. The reaction yield is ~40-50% 5-decene by fractional distillation.

The reaction scheme for the isomerization-hydroformylation (un-ligated) step is shown below.

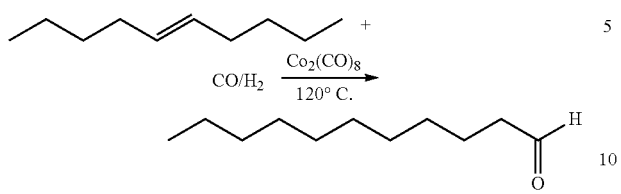

The isomerization-hydroformylation step can be performed as follows. A 5 L continuously stirred autoclave is charged with 190 g (1 mol) of 5-decene in 3.8 L of benzene and 4.27 g (0.0125 mol) of recently sublimed $Co_2(CO)_8$. The decene:cobalt molar ratio is maintained at ~40:1. The autoclave is pressurized with 3000 psig of a 1:1 mix of Syn-Gas mixture ($CO:H_2$) that is fed on demand and is heated at 120° C. until the reaction reaches 40-60% conversion, as monitored by aliquot sampling and GC-FID analysis. GC-FID reveals that, upon analysis of the reaction, greater than 50% of the internal olefin is converted to the primary aldehyde, 1-undecanal. The remainder of the product is a mixture of the various internal aldehydes declining in yield from the primary position. The products then can be individually isolated by fractional distillation to yield 90+% pure 1-undecanal.

The reaction scheme for the dehydroformylation step is shown below.

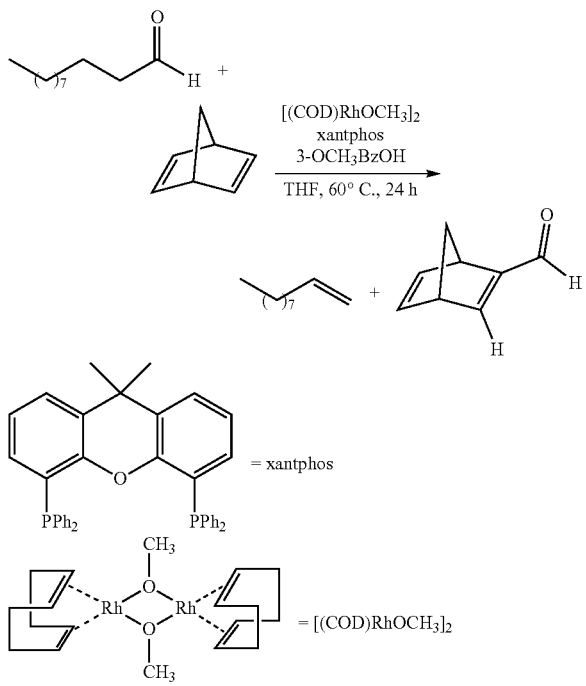

The dehydroformylation step to produce 1-decene can be performed as follows. In a drybox under an $N_2$ atmosphere, a 500 mL round bottom flask with a magnetic stir bar is charged with $[(COD)RhOCH_3]_2$ (2.72 g, 5 mmol), xantphos (5.79 g, 10 mmol), 3-methoxybenzoate (1.52 g, 10 mmol), 1-undecanal (170 g, 1 mol), and 250 mL (~3 mol) of THF. Norbornadiene (111 g, 1.2 mol) is then added last to the reaction mixture. The flask is placed in an aluminum block on a temperature controlled heating plate for 24 hr at 60° C. Reaction progress is monitored by taking aliquot samples and analyzing via GC-FID. Upon completion of the reaction, the reaction mixture is cooled, filtered, and the reaction product is distilled to isolate decene by fractional distillation. Product yield is 90+% decenes in a 95:5 ratio of 1-decene:2-decene, as determined by GC-FID.

Constructive Example 4

In accordance with the first process and the second process disclosed herein, Constructive Example 4 demonstrates the conversion of 1-hexene to 1-decene via a metathesis (heterogeneous), isomerization-hydroformylation (ligated), and dehydroformylation pathway as shown in the synthesis scheme below (where n=3).

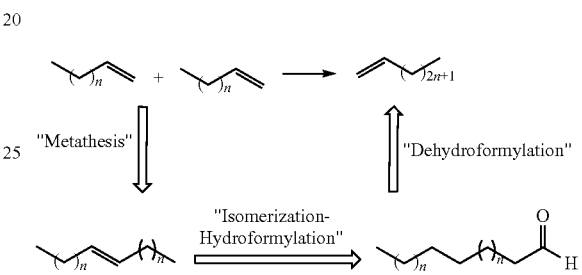

The reaction scheme for the heterogeneous metathesis step is shown below.

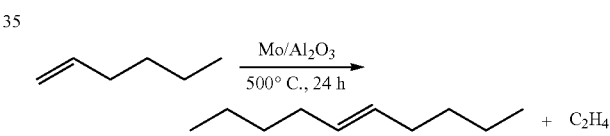

The metathesis step can be performed as follows. A 4-inch I.D. by 5-foot long stainless steel pipe is heated electrically for controlling reactor temperature and for catalyst activation/regeneration. The reactor contains 8.2 kg of molybdenum oxide-on-alumina catalyst (1.3% $MoO_3$, 0.07% $SiO_2$) from Nalco Chemical Company, consisting of ⅛" extrudate pellets treated with 1.5 wt. % KOH. The catalyst is regenerated by "burning off" polymer and hydrocarbons and holding the catalyst for 6 hr at 565° C. under air. The catalyst temperature is then reduced and the atmosphere changed to $N_2$. 1-hexene is distilled prior to use and charged to an olefin feed vessel. From the feed vessel, the 1-hexene is pumped at constant rate upflow through the catalyst bed. Reaction conditions are typically 87-110° C., at 20 psig pressure, with an LHSV of 0.5. The product then can be flowed into a product hold vessel, where ethylene is allowed to flash overhead. The crude product is then sent to a kettle bottom of a distillation column and distilled until the concentration of 5-decene in the kettle bottom reaches ~80%. At this point, approximately, 20 L of crude kettle product is obtained. The crude kettle product, approximately 73 kg, is loaded into the kettle of a 2" stainless steel distillation column with ¼" Octapac and distilled with 5-decene coming as the last cut at 86-89° C. and 50 mm Hg to yield approximately 41 kg of 5-decene with the following estimated specifications:

| | |
|---|---|
| Purity (wt. %) | 99.6 |
| cis 5-decene (wt. %) | 18.1 |
| trans 5-decene (wt. %) | 81.5 |
| Specific gravity (20/20° C.) | 0.742 |
| Refractive index ($N_D^{20}$) | 1.428 |
| Freezing point (° C.) | −75.8 |
| Boiling point (° C.) | 169.8 |

The reaction scheme for the isomerization-hydroformylation (ligated) step is shown below.

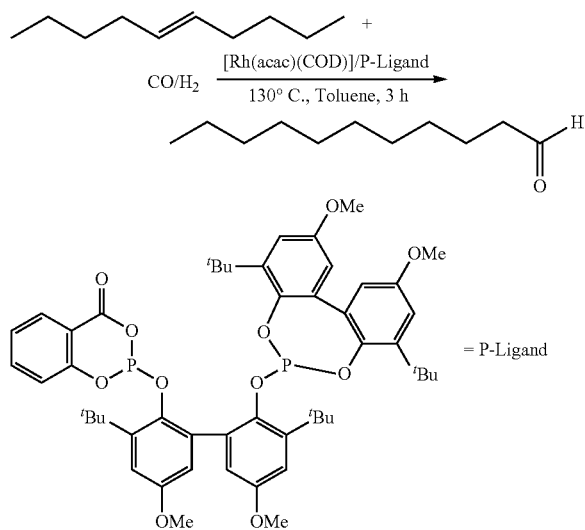

The isomerization-hydroformylation step can be performed as follows. A 1 L continuously stirred autoclave is charged with 600 mL of a 1.68 M solution of 5-decene (~190 g, 1 mol) in toluene, 0.2 g (0.63 mmol) of [Rh(acac)(COD)], and 5.8 g (6.4 mmol) of 3-aryloxy-1,3,2-dioxaphosphine-4-ones ligand, P-Ligand. The autoclave is pressurized with 300 psig of a 1:1 mix of syngas mixture (CO:$H_2$) that is fed on demand and is heated at 130° C. for 3 hr. GC-FID reveals that, upon analysis of the reaction, greater than 65% of the internal olefin is converted to the primary aldehyde, 1-undecanal. The remainder of the product is a mixture of the various internal aldehydes declining in yield from the primary position. The products then can be individually isolated by fractional distillation to yield 90+% pure 1-undecanal.

The reaction scheme for the dehydroformylation step is shown below.

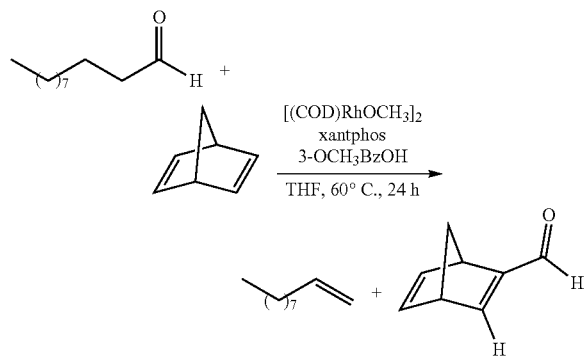

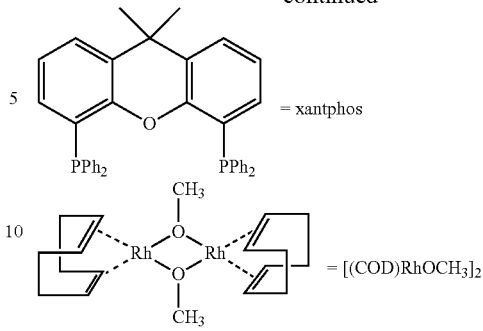

The dehydroformylation step to produce 1-decene can be performed as follows. In a drybox under an $N_2$ atmosphere, a 500 mL round bottom flask with a magnetic stir bar is charged with [(COD)RhOCH$_3$]$_2$(2.72 g, 5 mmol), xantphos (5.79 g, 10 mmol), 3-methoxybenzoate (1.52 g, 10 mmol), 1-undecanal (170 g, 1 mol), and 250 mL (~3 mol) of THF. Norbornadiene (111 g, 1.2 mol) is then added last to the reaction mixture. The flask is placed in an aluminum block on a temperature controlled heating plate for 24 hr at 60° C. Reaction progress is monitored by taking aliquot samples and analyzing via GC-FID. Upon completion of the reaction, the reaction mixture is cooled, filtered, and the reaction product is distilled to isolate decene by fractional distillation. Product yield is 90+% decenes in a 95:5 ratio of 1-decene:2-decene, as determined by GC-FID.

The invention is described herein with reference to numerous aspects and specific examples. Many variations will suggest themselves to those skilled in the art in light of the detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process (e.g., to make 1-octene/1-decene) comprising:
  a) separating a composition comprising an oligomer product, the oligomer product comprising from 15 to 80 mol % $C_6$ olefins, from 20 to 80 mol % $C_8$ olefins, and from 5 to 20 mol % $C_{10}$+ olefins, into
    i) a first oligomer composition comprising $C_6$ alkanes and at least 85 mol % $C_6$ olefins, the $C_6$ olefins comprising at least 80 mol % 1-hexene,
    ii) a second oligomer composition comprising at least 85 mol % $C_8$ olefins, the $C_8$ olefins comprising at least 85 mol % 1-octene, and
    iii) a heavies stream comprising $C_{10}$+ olefins;
  b) contacting a metathesis catalyst system with all or a portion of the first oligomer composition to form a first composition comprising $C_{10}$ linear internal olefins;
  c) contacting the $C_{10}$ linear internal olefins with an isomerization hydrofunctionalization catalyst system (such as a hydroformylation, a hydroboration, a hydrosilylation, a hydroalumination, or similar catalyst system that forms a C—X terminal bond) to form a second composition comprising a functionalized alkane;
  d) retro-hydrofunctionalizing the functionalized alkane (e.g., cleaving the C—X bond to form 1-decene) to form a third composition comprising 1-decene; and
  e) purifying the third composition to isolate a fourth composition comprising at least 90 mol % 1-decene.

Aspect 2. The process defined in aspect 1, wherein the oligomer product comprises from 30 to 70 mol % or from 35 to 65 mol % $C_6$ olefins (or any other minimum value, maximum value, or range described herein).

Aspect 3. The process defined in aspect 1 or 2, wherein the oligomer product comprises from 30 to 70 mol % or from 35 to 65 mol % $C_8$ olefins (or any other minimum value, maximum value, or range described herein).

Aspect 4. The process defined in any one of aspects 1-3, wherein the oligomer product comprises from 5 to 18 mol % or from 7 to 20 mol % $C_{10}+$ olefins (or any other minimum value, maximum value, or range described herein).

Aspect 5. The process defined in any one of aspects 1-4, wherein the first oligomer composition comprises at least 90 mol %, at least 93 mol %, or at least 95 mol % $C_6$ olefins (or any other minimum value, maximum value, or range described herein).

Aspect 6. The process defined in any one of aspects 1-5, wherein the first oligomer composition comprises from 0.5 to 12 mol %, from 1 to 10 mol %, from 1.5 to 8 mol %, or from 2 to 6 mol % $C_6$ alkanes (or any other minimum value, maximum value, or range described herein).

Aspect 7. The process defined in any one of aspects 1-6, wherein the $C_6$ olefins comprises at least 85 mol %, at least 90 mol %, at least 95 mol %, from 80 mol % to 98 mol %, from 80 mol % to 95 mol %, or from 85 mol % to 95 mol % 1-hexene (or any other minimum value, maximum value, or range described herein).

Aspect 8. The process defined in any one of aspects 1-7, wherein the $C_6$ olefins comprise from 0.1 to 10 mol %, from 0.5 to 8 mol %, or from 1 to 6 mol % internal and cyclic $C_6$ olefins (or any other minimum value, maximum value, or range described herein).

Aspect 9. The process defined in any one of aspects 1-8, wherein the second oligomer composition comprise at least 90 mol %, at least 95 mol %, or at least 97 mol % $C_8$ olefins (or any other minimum value, maximum value, or range described herein).

Aspect 10. The process defined in any one of aspects 1-9, wherein the $C_8$ olefins comprise at least 90 mol %, at least 95 mol %, or at least 97 mol % 1-octene (or any other minimum value, maximum value, or range described herein).

Aspect 11. The process defined in any one of aspects 1-10, further comprising a step of isolating a composition comprising at least 90 mol %, at least 93 mol %, or at least 96 mol % $C_{10}$ linear internal olefins from the first composition prior to step c) via any suitable technique or any technique disclosed herein, e.g., extraction, filtration, evaporation, distillation, or any combination thereof.

Aspect 12. The process defined in any one of aspects 1-11, further comprising a step of isolating a composition comprising at least 90 mol %, at least 93 mol %, or at least 96 mol % $C_{11}$ aldehydes from the second composition prior to step d) via any suitable technique or any technique disclosed herein, e.g., extraction, filtration, evaporation, distillation, or any combination thereof.

Aspect 13. The process defined in any one of aspects 1-12, further comprising a step of contacting the metathesis catalyst system with all or a portion of the $C_8$ olefin composition to form a $C_{14}$ olefin composition.

Aspect 14. The process defined in any one of aspects 1-13, further comprising a step of contacting the metathesis catalyst with a light oligomer composition comprising $C_6$ and $C_8$ olefins to form a composition comprising $C_{10}$-$C_{14}$ linear internal olefins.

Aspect 15. A process (e.g., to make 1-hexene/1-decene) comprising:

a) separating a composition comprising an oligomer product, the oligomer product comprising at least 85 mol % $C_6$ olefins and at least 5 mol % $C_8+$ olefins, into
  i) a first oligomer composition comprising $C_6$ alkanes and at least 90 mol % $C_6$ olefins, the $C_6$ olefins comprising at least 90 mol % 1-hexene, and
  ii) a heavies stream comprising $C_8+$ olefins;
b) contacting a metathesis catalyst system with all or a portion of the first oligomer composition to form a first composition comprising $C_{10}$ linear internal olefins;
c) contacting the $C_{10}$ linear internal olefins with an isomerization hydrofunctionalization catalyst system to form a second composition comprising a functionalized alkane;
d) retro-hydrofunctionalizing the functionalized alkane to form a third composition comprising 1-decene; and
e) purifying the third composition to isolate a fourth composition comprising at least 90 mol % 1-decene.

Aspect 16. The process defined in aspect 15, wherein the oligomer product comprises at least 85 mol %, at least 87 mol %, a least 90 mol %, at least 91 mol %, or at least 93 mol % $C_6$ olefins (or any other minimum value, maximum value, or range described herein).

Aspect 17. The process defined in aspect 15 or 16, wherein the oligomer product comprises from 5 to 15 mol % or from 5 to 12 mol % $C_8+$ olefins (or any other minimum value, maximum value, or range described herein).

Aspect 18. The process defined in any one of aspects 15-17, wherein the first oligomer composition comprises at least 94 mol %, at least 96 mol %, or at least 98 mol % $C_6$ olefins (or any other minimum value, maximum value, or range described herein).

Aspect 19. The process defined in any one of aspects 15-18, wherein the first oligomer composition comprises from 0.1 mol % to 1.5 mol %, from 0.15 mol % to 1 mol %, or from 0.2 mol % to 0.75 mol % $C_6$ alkanes (or any other minimum value, maximum value, or range described herein).

Aspect 20. The process defined in any one of aspects 15-19, wherein the $C_6$ olefins comprise at least 94 mol %, at least 96 mol %, or at least 98 mol % 1-hexene (or any other minimum value, maximum value, or range described herein).

Aspect 21. The process defined in any one of aspects 15-20, wherein the $C_6$ olefins comprise from 0.1 mol % to 3 mol %, from 0.2 mol % to 2 mol %, or from 0.25 mol % to 1 mol % internal and cyclic $C_6$ olefins (or any other minimum value, maximum value, or range described herein).

Aspect 22. The process defined in any one of aspects 15-21, further comprising a step of isolating a composition comprising at least 90 mol %, at least 93 mol %, or at least 96 mol % $C_{10}$ linear internal olefins from the first composition prior to step c) via any suitable technique or any technique disclosed herein, e.g., extraction, filtration, evaporation, distillation, or any combination thereof.

Aspect 23. The process defined in any one of aspects 15-22, further comprising a step of isolating a composition comprising at least 90 mol %, at least 93 mol %, or at least 96 mol % $C_{11}$ aldehydes from the second composition prior to step d) via any suitable technique or any technique disclosed herein, e.g., extraction, filtration, evaporation, distillation, or any combination thereof.

Aspect 24. The process defined in any one of aspects 1-23, wherein the fourth composition comprises at least 95 mol % or at least 98 mol % 1-decene (or any other minimum value, maximum value, or range described herein).

Aspect 25. The process defined in any one of aspects 1-24, wherein purifying in step e) comprises any suitable technique or any technique disclosed herein, e.g., extraction, filtration, evaporation, distillation, or any combination thereof.

Aspect 26. The process defined in any one of aspects 1-25, wherein the metathesis catalyst system is a metal oxide based metathesis catalyst system, a metal halide based metathesis catalyst system, a metal carbene based metathesis catalyst system, or any combination thereof.

Aspect 27. The process defined in aspect 26, wherein the metal oxide based metathesis catalyst system comprises cobalt oxide, molybdenum oxide, tungsten oxide, rhenium oxide, or any combination thereof.

Aspect 28. The process defined in aspect 27, wherein the metal oxide based metathesis catalyst system further comprises a support and/or a metal alkyl activator.

Aspect 29. The process defined in aspect 26, wherein the metal halide based metathesis catalyst system comprises a halide of tungsten, a halide of molybdenum, or any combination thereof.

Aspect 30. The process defined in aspect 29, wherein the metal halide based metathesis catalyst system further comprises a metal alkyl activator and/or oxygen or an alcohol.

Aspect 31. The process defined in aspect 26, wherein the metal carbene based metathesis catalyst system comprises tungsten, tantalum, osmium, molybdenum, ruthenium, or any combination thereof.

Aspect 32. The process defined in aspect 31, wherein the metal carbene based metathesis catalyst system further comprises a support.

Aspect 33. The process defined in any one of aspects 1-32, wherein the isomerization hydrofunctionalization catalyst system is a hydroformylation catalyst system comprising a rhodium compound, a cobalt compound, a ruthenium compound, an iridium compound, a platinum compound, a palladium compound, an iron compound, or any combination thereof.

Aspect 34. The process defined in any one of aspects 1-32, wherein the isomerization hydrofunctionalization catalyst system is a hydroformylation catalyst system comprising a cobalt compound, a hydroformylation catalyst system comprising a rhodium compound, or any combination thereof.

Aspect 35. The process defined in any one of aspects 1-34, wherein retro-hydrofunctionalizing comprises contacting the functionalized alkane with a dehydroformylation catalyst system comprising i) a transition metal compound, a phosphine, and a heteroatomic acid or heteroatomic acid derivative, or ii) a phosphine transition metal compound complex and a heteroatomic acid or heteroatomic acid derivative.

Aspect 36. The process defined in aspect 35, wherein the transition metal compound or the transition metal compound of the phosphine transition metal compound complex comprises a rhodium compound or an olefin rhodium alkoxide complex.

Aspect 37. The process defined in aspect 35, wherein the transition metal compound or the transition metal compound of the phosphine transition metal compound complex comprises a cyclodiene rhodium alkoxide complex.

Aspect 38. The process defined in any one of aspects 35-37, wherein the phosphine or the phosphine of the phosphine transition metal compound complex comprises any suitable alkyl phosphine and/or aryl phosphine.

Aspect 39. The process defined in any one of aspects 35-37, wherein the phosphine or the phosphine of the phosphine transition metal compound complex is a diphosphine having structure (I):

wherein:

$L^1$ is a linking group; and each R independently is H or a $C_1$ to $C_{18}$ hydrocarbyl group, a $C_1$ to $C_{18}$ hydrocarboxy group, or a $C_1$ to $C_{18}$ hydrocarbylaminyl group.

Aspect 40. The process defined in any one of aspects 35-37, wherein the phosphine or the phosphine of the phosphine transition metal compound complex is a diphosphine comprising a 1,6-bisphosphinylhexane, a substituted 1,6-bisphosphinylhexane, a (1,3-phenylenedi-1,1-ethanediyl)bis(phosphine), a substituted (1,3-phenylenedi-1,1-ethanediyl)bis(phosphine), a 1,8-anthracenediylbis(phosphine), a substituted 1,8-anthracenediylbis(phosphine), a 1,8-tetradecahydroanthracenediylbis(phosphine), or a substituted 1,8-tetradecahydroanthracenediylbis(phosphine), a (methylenedi-2,1-phenylene)bis(phosphine), a substituted (methylenedi-2,1-phenylene)bis(phosphine), a 9H-xanthene-4,5-diylbis(phosphine), a substituted 9H-xanthene-4,5-diylbis(phosphine), or a combination thereof.

Aspect 41. The process defined in any one of aspects 35-37, wherein the phosphine or the phosphine of the phosphine transition metal compound complex is a diphosphine having any one of the following structures:

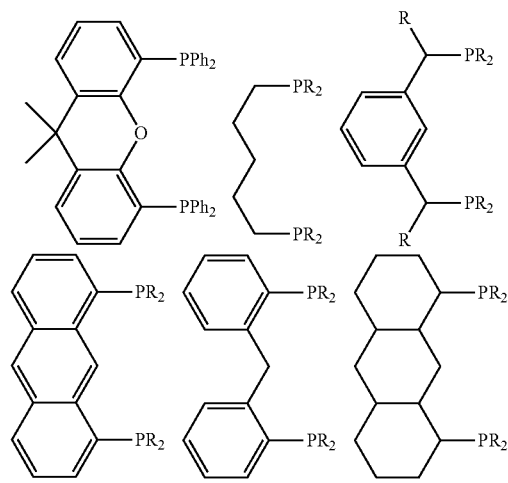

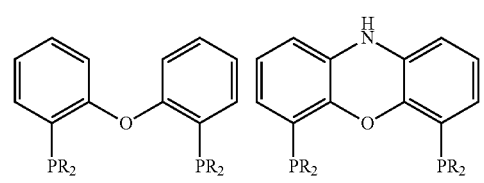

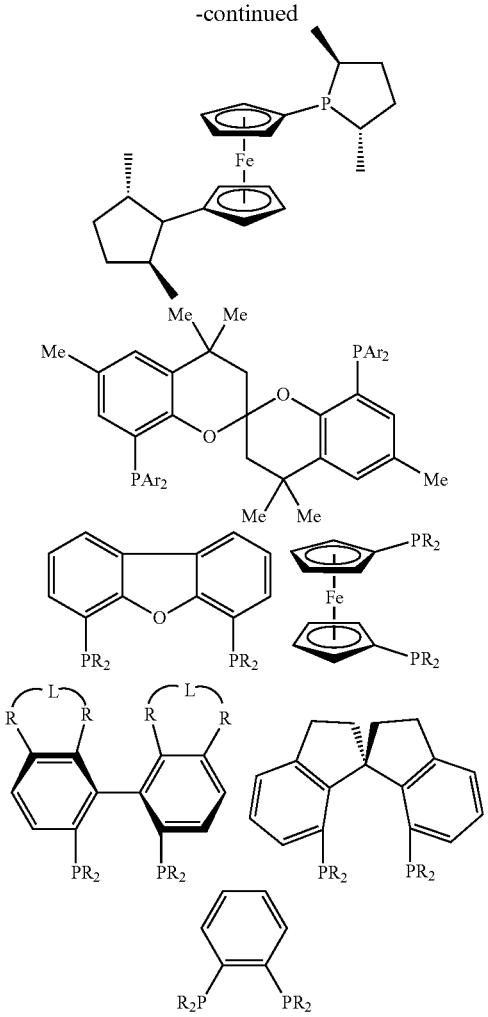

wherein:
Ph is a phenyl group;
Me is a methyl group;
Ar is $C_6$ to $C_8$ aromatic group;
each R independently is H or a $C_1$ to $C_{18}$ hydrocarbyl group, a $C_1$ to $C_1$ hydrocarboxy group, or a $C_1$ to $C_{18}$ hydrocarbylaminyl group; and
L is a $C_1$ to $C_{10}$ linking group.

Aspect 42. The process defined in any one of aspects 35-41, wherein the heteroatomic acid or heteroatomic acid derivative comprises a carboxylic acid, an alcohol, a mineral acid, an ammonium salt, an amine, a thiol, etc., or any combination thereof.

Aspect 43. The process defined in any one of aspects 35-41, wherein the heteroatomic acid or heteroatomic acid derivative comprises benzoic acid or a substituted benzoic acid, or a salt or ester of benzoic acid or a substituted benzoic acid.

Aspect 44. The process defined in any one of aspects 35-43, wherein the molar ratio of the transition metal of the transition metal compound to the phosphine (or diphosphine) is in a range from 0.2:1 to 5:1 (or any other minimum value, maximum value, or range described herein).

Aspect 45. The process defined in any one of aspects 35-44, wherein the molar ratio of the transition metal of the transition metal compound or the phosphine transition metal compound complex to the heteroatomic acid or heteroatomic acid derivative is in a range from 0.8:1 to 5:1 (or any other minimum value, maximum value, or range described herein).

Aspect 46. The process defined in any one of aspects 35-45, wherein the dehydroformylation catalyst system further comprises an acceptor.

Aspect 47. The process defined in aspect 46, wherein the acceptor (e.g., acceptor olefin) comprises a mono-olefin compound (e.g., ethylene, norbornene), a di-olefin compound (e.g., cyclooctadiene, norbornadiene), a tri-olefin compound (e.g., cyclododecatriene), or any combination thereof.

Aspect 48. The process defined in aspect 46 or 47, wherein the acceptor (e.g., acceptor olefin) is an aliphatic hydrocarbon compound.

Aspect 49. The process defined in aspect 46 or 47, wherein the acceptor (e.g., acceptor olefin) is a heteroatomic olefin compound, e.g., an enone, an enamine, an enol, an enamide (acrylamide), etc., or any combination thereof.

Aspect 50. The process defined in any one of aspects 46-49, wherein the acceptor (e.g., acceptor olefin) is a cyclic compound.

Aspect 51. The process defined in aspect 46, wherein the acceptor comprises an unsaturated triglyceride or an unsaturated natural source oil, e.g., soybean oil, corn oil, castor bean oil, canola oil, or any combination thereof.

Aspect 52. The process defined in aspect 46, wherein the acceptor comprises an aliphatic mono-olefin hydrocarbon, an aliphatic di-olefin hydrocarbon, an aliphatic tri-olefin hydrocarbon, or any combination thereof.

Aspect 53. The process defined in any one of aspects 1-52, wherein step d) is performed in a solvent (e.g., toluene, THF, dioxane).

Aspect 54. The process defined in any one of aspects 1-53, wherein step d) is performed at a temperature from 0° C. to 150° C. (or any other minimum temperature, maximum temperature, or temperature range described herein).

Aspect 55. The process defined in any one of aspects 46-54, wherein a molar ratio of the acceptor to the $C_{11}$ aldehyde is in a range from 0.2:1 to 1000:1 or from 0.5:1 to 5:1 (or any other minimum value, maximum value, or range described herein).

Aspect 56. The process defined in any one of aspects 35-55, wherein a molar ratio of the $C_{11}$ aldehyde to the transition metal of the transition metal compound or the phosphine transition metal compound complex is in a range from 2:1 to 1000:1 or from 10:1 to 250:1 (or any other minimum value, maximum value, or range described herein).

Aspect 57. The process defined in any one of aspects 1-56, wherein a molar yield of the 1-decene is at least 50%, at least 75%, or at least 90%, based on the $C_u$ linear aldehydes (or any other minimum value, maximum value, or range described herein).

Aspect 58. The process defined in any one of aspects 1-57, wherein the composition comprising the oligomer product is formed by contacting ethylene, a catalyst system or catalyst system components, optionally an organic reaction medium, and optionally hydrogen (e.g., in a reaction zone).

Aspect 59. A (1-octene/1-decene) manufacturing system comprising:
1) an ethylene oligomerization system configured to oligomerize ethylene in the presence of a catalyst system or catalyst system components to form a composition comprising an oligomer product, the oligomer product comprising from 20 to 80 mol % $C_6$ olefins, from 15 to 80 mol % $C_8$ olefins, and from 5 to 20 mol % $C_{10}+$ olefins;

2) a fractionation system configured to separate the composition comprising the oligomer product into i) a first oligomer composition comprising 1-hexene, ii) a second oligomer composition comprising 1-octene, and iii) a heavies stream comprising $C_{10}$+ olefins;

3) a metathesis system configured to contact a metathesis catalyst system with all or a portion of the first oligomer composition to form a first composition comprising $C_{10}$ linear internal olefins;

4) an isomerization hydrofunctionalization system configured to contact the $C_{10}$ linear internal olefins with an isomerization hydrofunctionalization catalyst system to form a second composition comprising a functionalized alkane;

5) a retro-hydrofunctionalization system configured to treat the functionalized alkane to form a third composition comprising 1-decene; and 6) a purification system configured to isolate a fourth composition comprising at least 90 mol % 1-decene from the third composition.

Aspect 60. A (1-hexene/1-decene) manufacturing system comprising:

1) an ethylene oligomerization system configured to oligomerize ethylene in the presence of a catalyst system or catalyst system components to form a composition comprising an oligomer product, the oligomer product comprising at least 85 mol % $C_6$ olefins and at least 5 mol % $C_8$+ olefins;

2) a fractionation system configured to separate the composition comprising the oligomer product into a first oligomer composition comprising 1-hexene and a heavies stream comprising $C_8$+ olefins;

3) a metathesis system configured to contact a metathesis catalyst system with all or a portion of the first oligomer composition to form a first composition comprising $C_{10}$ linear internal olefins;

4) an isomerization hydrofunctionalization system configured to contact the $C_{10}$ linear internal olefins with an isomerization hydrofunctionalization catalyst system to form a second composition comprising a functionalized alkane;

5) a retro-hydrofunctionalization system configured to treat the functionalized alkane to form a third composition comprising 1-decene; and 6) a purification system configured to isolate a fourth composition comprising at least 90 mol % 1-decene from the third composition.

Aspect 61. The manufacturing system defined in aspect 59 or 60, further comprising a metathesis purification system configured to isolate a composition comprising $C_{10}$ linear internal olefins from the first composition prior to the isomerization hydrofunctionalization system, wherein the purification system comprises extraction, filtration, evaporation, distillation, or any combination thereof.

Aspect 62. The manufacturing system defined in any one of aspects 59-61, further comprising an isomerization hydrofunctionalization purification system configured to isolate a composition comprising functionalized alkanes from the second composition prior to the retro-hydrofunctionalization system, wherein the purification system comprises extraction, filtration, evaporation, distillation, or any combination thereof.

Aspect 63. The process defined in aspect 58 or the manufacturing system defined in any one of aspects 59-62, wherein the catalyst system or catalyst system components comprise a heteroatomic ligand chromium compound complex and an alkylaluminum compound, or a heteroatomic ligand, a chromium compound, and an alkylaluminum compound.

What is claimed is:

1. A process comprising:
   a) separating a composition comprising an oligomer product, the oligomer product comprising from 15 to 80 mol % $C_6$ olefins, from 20 to 80 mol % $C_8$ olefins, and from 5 to 20 mol % $C_{10}$+ olefins, into
      i) a first oligomer composition comprising $C_6$ alkanes and at least 85 mol % $C_6$ olefins, the $C_6$ olefins comprising at least 80 mol % 1-hexene,
      ii) a second oligomer composition comprising at least 85 mol % $C_8$ olefins, the $C_8$ olefins comprising at least 85 mol % 1-octene, and
      iii) a heavies stream comprising $C_{10}$+ olefins;
   b) contacting a metathesis catalyst system with all or a portion of the first oligomer composition to form a first composition comprising $C_{10}$ linear internal olefins;
   c) contacting the $C_{10}$ linear internal olefins with an isomerization hydrofunctionalization catalyst system to form a second composition comprising a functionalized alkane;
   d) retro-hydrofunctionalizing the functionalized alkane to form a third composition comprising 1-decene; and
   e) purifying the third composition to isolate a fourth composition comprising at least 90 mol % 1-decene.

2. The process of claim 1, wherein the oligomer product comprises from 35 to 65 mol % $C_6$ olefins, from 35 to 65 mol % $C_8$ olefins, and from 5 to 18 mol % $C_{10}$+ olefins.

3. The process of claim 1, wherein:
   the first oligomer composition comprises from 1.5 to 8 mol % $C_6$ alkanes and at least 90 mol % $C_6$ olefins; and
   the $C_6$ olefins comprises at least 90 mol % 1-hexene and from 0.5 to 8 mol % internal and cyclic $C_6$ olefins.

4. The process of claim 1, wherein:
   the second oligomer composition comprises at least 95 mol % $C_8$ olefins; and
   the $C_8$ olefins comprise at least 95 mol % 1-octene.

5. The process of claim 1, further comprising a step of isolating an internal olefin composition comprising at least 90 mol % $C_{10}$ linear internal olefins from the first composition prior to step c).

6. The process of claim 1, wherein:
   step c) comprises contacting the $C_{10}$ linear internal olefins with a hydroformylation catalyst system, carbon monoxide, and hydrogen to form the second composition comprising $C_{11}$ aldehydes; and
   step d) comprises contacting the $C_{11}$ aldehydes with a dehydroformylation catalyst system to form the third composition comprising 1-decene.

7. The process of claim 6, further comprising a step of isolating an aldehyde composition comprising at least 90 mol % $C_1$ aldehydes from the second composition prior to step d).

8. The process of claim 6, wherein the dehydroformylation catalyst system comprises i) a transition metal compound, a phosphine, and a heteroatomic acid or heteroatomic acid derivative, or ii) a phosphine transition metal compound complex and a heteroatomic acid or heteroatomic acid derivative.

9. The process of claim 1, further comprising a step of contacting the metathesis catalyst system with all or a portion of the second oligomer composition to form a $C_{14}$ olefin composition.

10. The process of claim 1, wherein the fourth composition comprises at least 95 mol % 1-decene.

11. A process comprising:
a) separating a composition comprising an oligomer product, the oligomer product comprising at least 85 mol % $C_6$ olefins and at least 5 mol % $C_8+$ olefins, into
  i) a first oligomer composition comprising $C_6$ alkanes and at least 90 mol % $C_6$ olefins, the $C_6$ olefins comprising at least 90 mol % 1-hexene, and
  ii) a heavies stream comprising $C_8+$ olefins;
b) contacting a metathesis catalyst system with all or a portion of the first oligomer composition to form a first composition comprising $C_{10}$ linear internal olefins;
c) contacting the $C_{10}$ linear internal olefins with an isomerization hydrofunctionalization catalyst system to form a second composition comprising a functionalized alkane;
d) retro-hydrofunctionalizing the functionalized alkane to form a third composition comprising 1-decene; and
e) purifying the third composition to isolate a fourth composition comprising at least 90 mol % 1-decene.

12. The process of claim 11, wherein the oligomer product comprises at least 90 mol % $C_6$ olefins.

13. The process of claim 11, wherein:
the first oligomer composition comprises at least 94 mol % $C_6$ olefins; and
the $C_6$ olefins comprises at least 96 mol % 1-hexene.

14. The process of claim 11, further comprising a step of isolating an internal olefin composition comprising at least 90 mol % $C_{10}$ linear internal olefins from the first composition prior to step c).

15. The process of claim 11, wherein:
step c) comprises contacting the $C_{10}$ linear internal olefins with a hydroformylation catalyst system, carbon monoxide, and hydrogen to form the second composition comprising $C_{11}$ aldehydes;
step d) comprises contacting the $C_{11}$ aldehydes with a dehydroformylation catalyst system to form the third composition comprising 1-decene; and
the process further comprises a step of isolating an aldehyde composition comprising at least 90 mol % $C_{11}$ aldehydes from the second composition prior to step d).

16. A 1-octene/1-decene manufacturing system comprising:
1) an ethylene oligomerization system configured to oligomerize ethylene in the presence of a catalyst system or catalyst system components to form a composition comprising an oligomer product, the oligomer product comprising from 15 to 80 mol % $C_6$ olefins, from 20 to 80 mol % $C_8$ olefins, and from 5 to 20 mol % $C_{10}+$ olefins;
2) a fractionation system configured to separate the composition comprising the oligomer product into i) a first oligomer composition comprising 1-hexene, ii) a second oligomer composition comprising 1-octene, and iii) a heavies stream comprising $C_{10}+$ olefins;
3) a metathesis system configured to contact a metathesis catalyst system with all or a portion of the first oligomer composition to form a first composition comprising $C_{10}$ linear internal olefins;
4) an isomerization hydrofunctionalization system configured to contact the $C_{10}$ linear internal olefins with an isomerization hydrofunctionalization catalyst system to form a second composition comprising a functionalized alkane;
5) a retro-hydrofunctionalization system configured to treat the functionalized alkane to form a third composition comprising 1-decene; and
6) a purification system configured to isolate a fourth composition comprising at least 90 mol % 1-decene from the third composition.

17. The manufacturing system of claim 16, further comprising a metathesis purification system configured to isolate a composition comprising $C_{10}$ linear internal olefins from the first composition prior to the isomerization hydrofunctionalization system.

18. The manufacturing system of claim 16, further comprising a isomerization hydrofunctionalization purification system configured to isolate a composition comprising functionalized alkanes from the second composition prior to the retro-hydrofunctionalization system.

19. The manufacturing system of claim 16, wherein the catalyst system or catalyst system components comprise a heteroatomic ligand chromium compound complex and an alkylaluminum compound, or a heteroatomic ligand, a chromium compound, and an alkylaluminum compound.

20. A 1-hexene/1-decene manufacturing system comprising:
1) an ethylene oligomerization system configured to oligomerize ethylene in the presence of a catalyst system or catalyst system components to form a composition comprising an oligomer product, the oligomer product comprising at least 85 mol % $C_6$ olefins and at least 5 mol % $C_8+$ olefins;
2) a fractionation system configured to separate the composition comprising the oligomer product into a first oligomer composition comprising 1-hexene and a heavies stream comprising $C_8+$ olefins;
3) a metathesis system configured to contact a metathesis catalyst system with all or a portion of the first oligomer composition to form a first composition comprising $C_{10}$ linear internal olefins;
4) an isomerization hydrofunctionalization system configured to contact the $C_{10}$ linear internal olefins with an isomerization hydrofunctionalization catalyst system to form a second composition comprising a functionalized alkane;
5) a retro-hydrofunctionalization system configured to treat the functionalized alkane to form a third composition comprising 1-decene; and
6) a purification system configured to isolate a fourth composition comprising at least 90 mol % 1-decene from the third composition.

21. The process of claim 11, wherein the fourth composition comprises at least 95 mol % 1-decene.

22. The process of claim 11, wherein:
step c) comprises contacting the $C_{10}$ linear internal olefins with a hydroformylation catalyst system, carbon monoxide, and hydrogen to form the second composition comprising $C_{11}$ aldehydes; and
step d) comprises contacting the $C_{11}$ aldehydes with a dehydroformylation catalyst system to form the third composition comprising 1-decene.

23. The process of claim 22, further comprising a step of isolating an aldehyde composition comprising at least 93 mol $C_{11}$ aldehydes from the second composition prior to step d).

24. The process of claim 22, wherein the dehydroformylation catalyst system comprises i) a transition metal compound, a phosphine, and a heteroatomic acid or heteroatomic acid derivative, or ii) a phosphine transition metal compound complex and a heteroatomic acid or heteroatomic acid derivative.

25. The manufacturing system of claim 16, further comprising a recycle stream from the retro-hydrofunctionalization system for recycling carbon monoxide and/or hydrogen to the isomerization hydrofunctionalization system.

26. The manufacturing system of claim 16, further comprising a metathesis purification system configured to isolate a composition comprising $C_{10}$ linear internal olefins from the first composition prior to the isomerization hydrofunctionalization system.

27. The manufacturing system of claim 20, further comprising an isomerization hydrofunctionalization purification system configured to isolate a composition comprising functionalized alkanes from the second composition prior to the retro-hydrofunctionalization system.

28. The manufacturing system of claim 20, further comprising a metathesis purification system configured to isolate a composition comprising Cio linear internal olefins from the first composition prior to the isomerization hydrofunctionalization system.

29. The manufacturing system of claim 20, further comprising a recycle stream from the retro-hydrofunctionalization system for recycling carbon monoxide and/or hydrogen to the isomerization hydrofunctionalization system.

30. The manufacturing system of claim 20, wherein the catalyst system or catalyst system components comprise a heteroatomic ligand chromium compound complex and an alkylaluminum compound, or a heteroatomic ligand, a chromium compound, and an alkylaluminum compound.

\* \* \* \* \*